(12) United States Patent
Sholev et al.

(10) Patent No.: US 9,770,248 B2
(45) Date of Patent: Sep. 26, 2017

(54) CIRCULAR BONE TUNNELING DEVICE

(75) Inventors: Mordehai Sholev, Amikam (IL); Gilad Lavi, Lezion (IL)

(73) Assignee: MININVASIVE LTD., Tel Aviv (IL)

( * ) Notice: Subject to any disclaimer, the term of this patent is extended or adjusted under 35 U.S.C. 154(b) by 1031 days.

(21) Appl. No.: 13/809,562

(22) PCT Filed: Jul. 11, 2011

(86) PCT No.: PCT/IL2011/000549
§ 371 (c)(1),
(2), (4) Date: Mar. 22, 2013

(87) PCT Pub. No.: WO2012/007941
PCT Pub. Date: Jan. 19, 2012

(65) Prior Publication Data
US 2013/0178854 A1    Jul. 11, 2013

Related U.S. Application Data

(60) Provisional application No. 61/363,247, filed on Jul. 11, 2010.

(51) Int. Cl.
*A61B 17/062* (2006.01)
*A61B 17/16* (2006.01)
(Continued)

(52) U.S. Cl.
CPC .......... *A61B 17/16* (2013.01); *A61B 17/0469* (2013.01); *A61B 17/0482* (2013.01);
(Continued)

(58) Field of Classification Search
CPC ... A61B 17/82; A61B 17/823; A61B 17/0469; A61B 17/0057; A61B 17/04;
(Continued)

(56) References Cited

U.S. PATENT DOCUMENTS 2,579,192 A    12/1951   Kohl
5,250,055 A    10/1993   Moore et al.
(Continued)

FOREIGN PATENT DOCUMENTS

CN    101193600 B    9/2010
EP    1898812        3/2008
(Continued)

OTHER PUBLICATIONS

U.S. Appl. No. 61/636,751, filed Apr. 23, 2012.
(Continued)

*Primary Examiner* — Todd E Manahan
*Assistant Examiner* — Jessica Weiss
(74) *Attorney, Agent, or Firm* — Sughrue Mion, PLLC

(57) ABSTRACT

An adjustable suture passer for use in arthroscopic surgery is disclosed. In a preferred embodiment, the adjustable suture passer comprises a head that describes a semicircular arc, an elongate body, a support element, and driving and control mechanisms. The head is adapted to accommodate a surgical needle and a guide wire. When the adjustable suture passer is activated, the needle is driven with sufficient force to penetrate bone. Use of the adjustable suture passer thus enables surgical attachment of soft tissue to bone without any necessity for a separate anchor.

11 Claims, 19 Drawing Sheets

(51) Int. Cl.
*A61B 17/04* (2006.01)
*A61B 17/06* (2006.01)
*A61B 17/34* (2006.01)
*A61B 17/00* (2006.01)
*A61B 17/29* (2006.01)

(52) U.S. Cl.
CPC ........ *A61B 17/062* (2013.01); *A61B 17/0625* (2013.01); *A61B 17/06066* (2013.01); *A61B 17/3472* (2013.01); *A61B 2017/00398* (2013.01); *A61B 2017/00477* (2013.01); *A61B 2017/061* (2013.01); *A61B 2017/06042* (2013.01); *A61B 2017/2931* (2013.01)

(58) Field of Classification Search
CPC .............. A61B 17/0483; A61B 17/062; A61B 17/0625; A61B 17/00663; A61B 2017/047; A61F 2/95; B26F 2001/402
USPC .................. 606/228–233, 138–150, 74, 103
See application file for complete search history.

(56) References Cited

U.S. PATENT DOCUMENTS

| | | | |
|---|---|---|---|
| 5,387,221 A | 2/1995 | Bisgaard | |
| 5,499,991 A | 3/1996 | Garman et al. | |
| 5,665,096 A * | 9/1997 | Yoon ................ | A61B 17/0469 606/139 |
| 5,681,333 A | 10/1997 | Burkhart et al. | |
| 5,961,530 A | 10/1999 | Moore | |
| 6,328,744 B1 | 12/2001 | Harari | |
| 6,443,963 B1 | 9/2002 | Baldwin | |
| 6,523,417 B1 | 2/2003 | Donahue | |
| 7,029,479 B2 | 4/2006 | Tallarida | |
| 7,097,648 B1 * | 8/2006 | Globerman ........ | A61B 17/1637 606/247 |
| 7,166,116 B2 | 1/2007 | Lizardi et al. | |
| 7,662,171 B2 | 2/2010 | West, Jr. | |
| 8,282,657 B2 * | 10/2012 | McClurg ............ | A61B 17/0469 606/139 |
| 2002/0040227 A1 * | 4/2002 | Harari ................ | A61B 17/0625 606/153 |
| 2003/0078599 A1 | 4/2003 | O'Quinn | |
| 2006/0195121 A1 | 8/2006 | Chu | |
| 2006/0271060 A1 | 11/2006 | Gordon | |
| 2007/0005067 A1 | 1/2007 | Dross | |
| 2007/0179509 A1 | 8/2007 | Nagata et al. | |
| 2008/0109015 A1 * | 5/2008 | Chu .................. | A61B 17/0469 606/139 |
| 2008/0228224 A1 | 9/2008 | Sauer | |
| 2009/0012538 A1 * | 1/2009 | Saliman ............ | A61B 17/0491 606/145 |
| 2009/0062819 A1 | 3/2009 | Burkhart | |
| 2009/0069823 A1 | 3/2009 | Foerster | |
| 2009/0105729 A1 | 4/2009 | Zentgraf | |
| 2009/0105743 A1 | 4/2009 | Chu | |
| 2009/0131956 A1 | 5/2009 | Dewey | |
| 2009/0138029 A1 * | 5/2009 | Saliman ............ | A61B 17/0469 606/144 |
| 2009/0312782 A1 | 12/2009 | Park | |
| 2010/0076436 A1 | 3/2010 | Hajianpour | |
| 2010/0106194 A1 | 4/2010 | Bonutti et al. | |
| 2010/0152751 A1 | 6/2010 | Meade et al. | |
| 2010/0191248 A1 * | 7/2010 | Mehta ................ | A61B 17/1631 606/96 |
| 2010/0198258 A1 | 8/2010 | Heaven et al. | |
| 2010/0318139 A1 | 12/2010 | Beauchamp | |
| 2011/0022063 A1 | 1/2011 | McClurg | |
| 2011/0106124 A1 | 5/2011 | Beauchamp | |
| 2012/0239085 A1 | 9/2012 | Schlotterback et al. | |
| 2012/0323248 A1 | 12/2012 | Dross | |
| 2013/0123810 A1 | 5/2013 | Brown et al. | |
| 2014/0303625 A1 | 10/2014 | Sholev et al. | |

FOREIGN PATENT DOCUMENTS

| | | |
|---|---|---|
| EP | 1970016 | 9/2008 |
| EP | 2698128 | 2/2014 |
| JP | 1996-033635 | 2/1996 |
| JP | 1996-509918 | 10/1996 |
| JP | 2003-501132 | 1/2003 |
| JP | 2008-510526 | 4/2008 |
| JP | 2008546489 A | 12/2008 |
| WO | 96/27331 | 9/1996 |
| WO | 97/47246 | 12/1997 |
| WO | 0074578 A2 | 12/2000 |
| WO | 02/007609 | 1/2002 |
| WO | 2009/107121 | 9/2009 |
| WO | 2010/056785 | 5/2010 |
| WO | 2010/056786 | 5/2010 |
| WO | 2010/056787 | 5/2010 |
| WO | 2011/160166 | 12/2011 |
| WO | 2012/007941 | 1/2012 |
| WO | 2013/027209 | 2/2013 |
| WO | 2013/027210 | 2/2013 |
| WO | 2013071234 | 5/2013 |
| WO | 2013/102909 | 7/2013 |
| WO | 2014/147619 | 9/2014 |

OTHER PUBLICATIONS

U.S. Appl. No. 61/584,267, filed Jan. 8, 2012.
U.S. Appl. No. 61/526,717, filed Aug. 24, 2011.
U.S. Appl. No. 61/363,247, filed Jul. 11, 2010.
U.S. Appl. No. 61/714,813, filed Oct. 17, 2012.
An International Search Report and a Written Opinion both dated Jan. 23, 2013, which issued during the prosecution of Applicant's PCT/IL2012/000318.
An International Search Report and a Written Opinion both dated Dec. 5, 2011, which issued during the prosecution of Applicant's PCT/IL2011/000549.
An International Search Report and a Written Opinion both dated May 10, 2013 which issued during the prosecution of Applicant's PCT/IL2013/050030.
An International Search Report dated Jan. 8, 2013 which issued during the prosecution of Applicant's PCT/IL2012/000319.
An International Preliminary Report dated Mar. 6, 2014 which issued during the prosecution of Applicant's PCT/IL2012/000319.
Written Opinion dated Jan. 8, 2013 which issued during the prosecution of Applicant's PCT/IL2012/000319.
An International Preliminary Report dated Mar. 6, 2014 which issued during the prosecution of Applicant's PCT/IL2012/000318.
An Office Action dated Apr. 5, 2014 which issued during the prosecution of Australian Patent Application No. 2011277949.
An English translation of an Office Action dated Mar. 24, 2015, which issued during the prosecution of Japanese Patent Application No. 519213/2013.
An English translation of an Office Action dated Jul. 3, 2014 which issued during the prosecution of Chinese Patent Application 2011800437287.
An International Search Report and Written Opinion both dated Jul. 11, 2014, which issued during the prosecution of Applicant's PCT/IL 14/50299.
An International Preliminary Search Report dated Aug. 26, 2014, which issued during the prosecution of Applicant's PCT/IL2013/050030.
European Search Report dated Jun. 11, 2015 which issued during the prosecution of Applicant's European App No. 12826407.
An Office Action dated Feb. 18, 2016 which issued during the prosecution of Australian Patent Application No. 2012298197.
An International Search Report and a Written Opinion both dated Mar. 10, 2016, which issued during the prosecution of Applicant's PCT/IL2015/050923.
European Search Report dated Jan. 27, 2016 which issued during the prosecution of Applicant's European App No. 13733888.
An Invitation to pay additional fees dated Dec. 23, 2015, which issued during the prosecution of Applicant's PCT/IL2015/050923.

(56) References Cited

OTHER PUBLICATIONS

An Office Action dated Jan. 5, 2016, which issued during the prosecution of Japanese Patent Application No. 2013-519213.
An Office Action dated Jul. 11, 2016 which issued during the prosecution of Australian Patent Application No. 2012298197.
An International Search Report and a Written Opinion both dated Jun. 9, 2016, which issued during the prosecution of Applicant's PCT/IL2015/050978.
An Office Action dated Jun. 27, 2016 which issued during the prosecution of Australian Patent Application No. 2015202032.
An Office Action dated May 24, 2016 which issued during the prosecution of Chinese Patent Application No. 2013800124154.
Translation of Notice of Reasons for Refusal, mailed Sep. 6, 2016, issued in corresponding JP Application No. 2014-526597, 5 pages in English.
An Office Action dated Oct. 13, 2016, which issued during the prosecution of U.S. Appl. No. 14/240,082.
European Search Report dated Jan. 17, 2017, which issued during the prosecution of Applicant's European App No. 14769413.7.
An Office Action dated Mar. 21, 2017, which issued during the prosecution of U.S. Appl. No. 14/240,227.
An Office Action dated Mar. 20, 2017, which issued during the prosecution of U.S. Appl. No. 14/240,082.
An Office Action dated Nov. 22, 2016 which issued during the prosecution of Japanese Patent Application No. 550801/2014.
European Search Report dated May 11, 2017, which issued during the prosecution of Applicant's European App No. 11806391.6.

\* cited by examiner

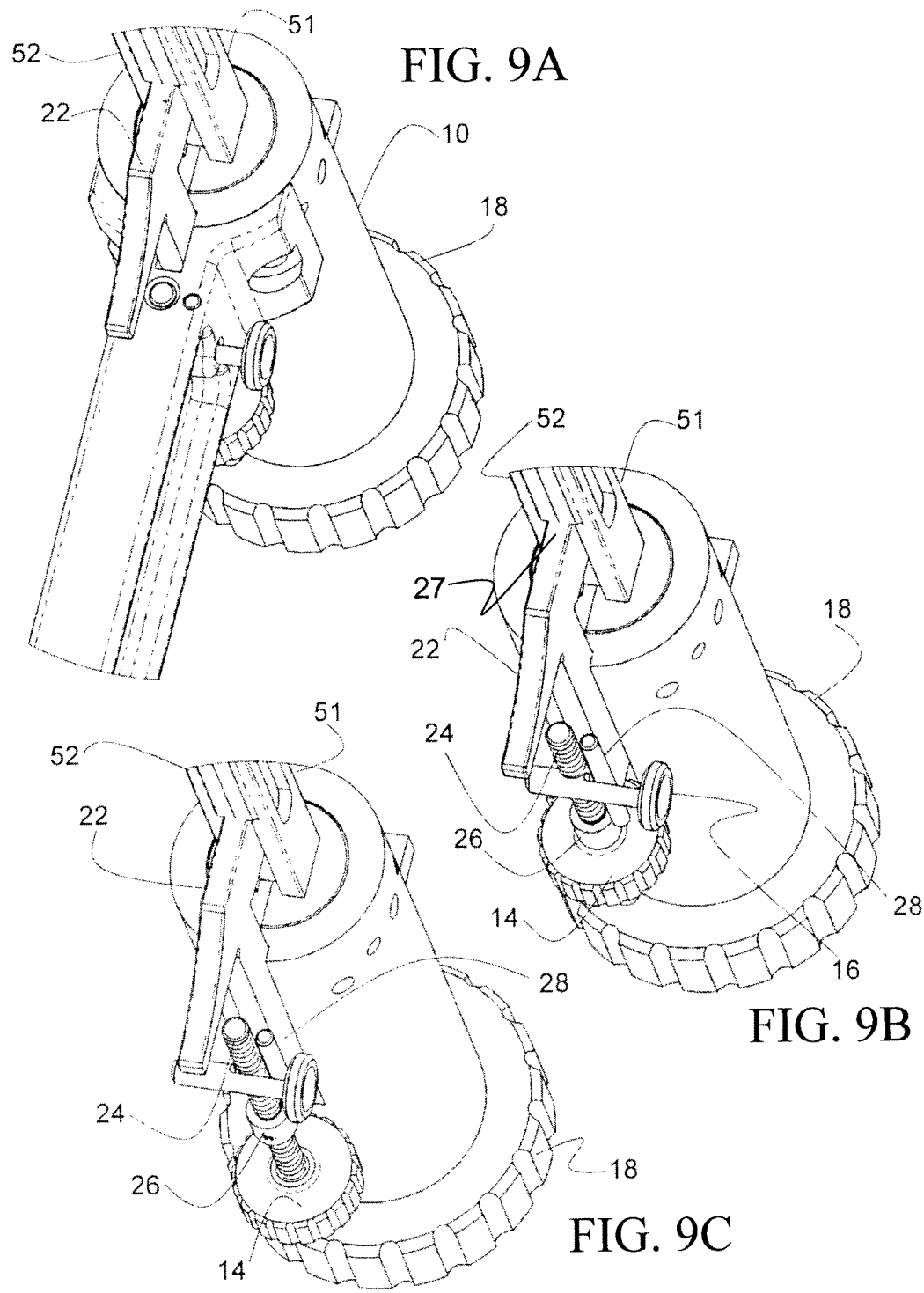

CIRCULAR BONE TUNNELING DEVICE

CROSS REFERENCE TO RELATED APPLICATIONS

This application is a National Stage of International Application No. PCT/IL2011/000549, filed on Jul. 11, 2011, which claims priority from U.S. Patent Provisional Application No. 61/363,247, filed Jul. 11, 2010, the contents of all of which are incorporated herein by reference in their entirety.

FIELD OF THE INVENTION

This invention generally relates to a bone tunneling device and an adjustable suture passer for use in arthroscopic surgery. Specifically, it relates to suture passers that are capable of passing a suture through a bone directly without need for a separate anchor embedded in the bone and/or preceding action of tunneling through the bone (e.g. by drilling or any other act followed by removal of bone debris), and then a suture may be passed through said tunnels The present invention provides an adjustable suture passer, adapted to enable passage of a suture through a bone while grasping the circumference of the same and without drilling through the same. Furthermore, the present invention provides an adjustable suture passer which causes no fractures or which does not significantly weaken the bone.

BACKGROUND OF THE INVENTION

Reattachment of a ligament to a bone in arthroscopic procedures such as, for example, repair of a torn rotator cuff typically involves two steps. First, an anchor is inserted into the bone. Then, the ligament is attached to the bone by passing a suture through the ligament tissue and then through the anchor, thereby tying the ligament to the bone.

There are several drawbacks to this method. First, two separate actions must be performed in order to attach the ligament to the bone, namely, insertion of the anchor into the bone and suturing of the ligament. The necessary involvement of at least two separate sets of tools inherently complicates the surgical procedure, when compared to performing the procedure while using a single tool.

In addition, placement of the anchor may require drilling into the bone, which creates debris that must be removed and can increase the stress on the bone. The procedures described above often require large access ports and/or open surgery to enable the positioning and actuation of the required tools.

Methods that do not require an anchor generally require creation of a plurality of bores in the bone. U.S. Pat. No. 6,523,417 discloses a method for suturing soft tissue to a bone in which a hole is drilled into the bone and a slit cut into it. PCT Pat. Application WO09/107121 discloses a method of suturing soft tissue to a bone in which two bores are made in the bone at an angle, preferably 70°. PCT Pat. Applications WO10/056785, WO10/056786, and WO10/056787 disclose suture anchoring systems in which two orthogonal bores are made in the bone. A major disadvantage of these methods is that the presence of a plurality of bores at an angle significantly weakens the bone, increasing the likelihood of later injury, fractures and eventually weakening of the bone. The main disadvantage in said publication is that these methods require highly invasive surgery in order to allow access and actuation of tools used in the procedure.

U.S. Pat. No. 6,328,744 discloses a bone suturing device in which a needle enters a bone at a non-perpendicular angle and a curved path due to the force exerted on the needle by a hinged handle. In preferred embodiments of the invention, a second needle is used as well and the bore created from two sides. While the purpose of the second needle is to increase the pressure used by the first needle to enter the bone rather than to push the bone away, the amount of stabilization actually performed by the second needle is limited because the two needles enter the bone from the same side. Thus. It is a long felt need to provide a device which will enable stabilization to said bone.

There is thus a long-felt need for a device that can enable direct attachment of the ligament and the bone by passing the suture through the bone without any need for a separate anchor or for weakening the bone by drilling two orthogonal holes through it and that supports the bone from a side other than that through which the needle enters.

Yet more, it is a further long-felt need for a device that can securely passes a suture so as to provide said attachment.

Yet more, it is a further long felt need to provide a tool that can be applied to the bone surface through a small minimally invasive incision and then be converted into a second larger profile, that enables fixation to a bone surface along the path of an arc within the bone without enlargement of the access incision point.

SUMMARY OF THE INVENTION

The arthroscopic bone tunneling device disclosed in the present invention is designed to enable bone tunnel formation, passage of a suture through the tunnel and fixation of a muscle or ligament to the bone. The device comprises means for ejecting a needle with sufficient force that the needle can penetrate bone. This is made possible by fixation of the needle applicator to the bone with sufficient stability to allow the application of the force required to penetrate the bone. If the needle is attached to a guide wire, the guide wire can be used to carry a suture through the soft tissue and the bone, thus enabling attachment of the soft tissue to the bone without any need for a separate anchor.

In general, the arthroscopic bone tunneling device disclosed in the present invention fixates itself to an essentially circular bone structure (i.e., to the circumference of a bone). The penetration of the needle is then actuated at an approximately perpendicular angle to the bone. Thereafter, an arched tunnel is formed which connects two points along the circumference.

The present invention provides an arthroscopic bone tunneling device which tunnels through an arc defined by two points on the circumference of a bone. The tunnel is formed by penetration of a rigid needle device without the need to drill.

According to one embodiment, the arthroscopic bone tunneling device is connected to a suture which is simultaneously passed through the tunnel formed. The sutures can then be used to fix a tissue, muscle or ligament to a bone.

The arthroscopic bone tunneling device comprises, inter alia, a rigid needle which penetrates the bone at a first point along the circumference of the same; and an extendable and retractable support element (will be disclosed hereinafter) which provides counter force at a second point along the circumference of the bone close to where the arc (i.e., the needle) exits the bone. Such an extendable and retractable support element enables the tunneling without drilling.

No anchors are required since the sutures are fixed through the arc formed in the bone in a full loop configuration.

The extendable and retractable support element (which provides the counter force—fixates the bone tunneling device onto the bone while tunneling is being performed.

The extendable and retractable support element is reconfigurable from at least one extended configuration to at least one retracted configuration.

The entire unit has a low profile when entering the incision (when the extendable and retractable support element is in its retracted configuration) and a slightly larger profile when the fixation device is deployed (i.e., when the extendable and retractable support element is in its extended configuration).

Thus the unit is the first truly minimally invasive tool for rotary cuff repair and does not require large sub-dermal space to deploy its streamline, no drilling configuration.

As used herein the term "ejecting" refers to an act of penetration or tunneling of an element through the bone without any drilling or removing bone's material (e.g. debris).

It is thus one object of the present invention to disclose a circular bone tunneling device (and an adjustable suture passer), for use in arthroscopic surgery, comprising: (a) a hollow elongate body comprising a hollow elongate body head; said hollow elongate body head defining a rigid circular arc; said hollow elongate body comprising a surgical needle adapted to tunnel through a bone along a path formed by said rigid circular arc; and, (b) an extendable and retractable support element, reconfigurable from at least one extended configuration to at least one retracted configuration.

It is emphasized that said support element, in said extended configuration, is adapted to be located along said path formed by said rigid circular arc.

It is further emphasized that said support element, in said extended configuration, and said hollow elongate head body are adapted to grasp said bone from at least two points along the circumference of said bone.

It is another object of the present invention to disclose the curved/circular bone tunneling device and\or an adjustable suture passer as defined above, wherein said surgical needle is a rigid surgical needle.

It is another object of the present invention to disclose the curved/circular bone tunneling device and\or an adjustable suture passer as defined above, wherein the surgical needle is rigid and is either straight or substantially shaped as a circular arc.

It is another object of the present invention to disclose the curved/circular bone tunneling device and\or an adjustable suture passer as defined above, wherein said rigid circular hollow tube is sufficiently rigid so that its circular shape is maintained as it penetrates said bone along said circular arc.

It is another object of the present invention to disclose the curved/circular bone tunneling device and\or an adjustable suture passer as defined above, wherein said hollow elongate body is characterized by having a top side and an underside, and further comprising a shaft (50); further wherein said hollow elongate body head located at the distal end of said shaft and defining said rigid circular arc with the concave side of said arc forming said underside of said hollow elongate body head; and, comprising at its distal end an orifice of diameter sufficient to permit passage of said surgical needle.

It is another object of the present invention to disclose the curved/circular bone tunneling device and\or an adjustable suture passer as defined above, wherein said extendable and retractable support element (54) is attached to the distal end of said shaft and disposed such that when said support element is extended, it opposes the underside of said curved hollow elongate body head and its distal end is located along the path formed by said rigid circular arc.

It is another object of the present invention to disclose the curved/circular bone tunneling device and\or an adjustable suture passer as defined above, additionally comprising a rigid circular hollow tube (34) (refers hereinafter as circular rigid hollow tube or hollow tube) adapted to be reversibly attached to said needle and to carry at least one guide wire (130), said rigid circular hollow tube movably disposed at least partially within said hollow body such that said rigid circular hollow tube can move along the proximal-distal direction of said body and through an orifice in said hollow elongate body head.

It is another object of the present invention to disclose the curved/circular bone tunneling device and\or an adjustable suture passer as defined above, wherein said rigid circular hollow tube is sufficiently rigid so that its circular shape is maintained as it penetrates said bone along said circular arc.

It is another object of the present invention to disclose the curved/circular bone tunneling device and\or an adjustable suture passer as defined above, additionally comprising a support element driving mechanism, adapted, upon activation of a support element control, to drive the motion of said support element.

It is another object of the present invention to disclose a curved/circular bone tunneling device and\or an adjustable suture passer for use in arthroscopic surgery, comprising: (a) a hollow elongate body having a top side and an underside, comprising a hollow elongate body head (90) and a shaft (50), said hollow elongate body head located at the distal end of said shaft and providing an essentially circular arc with the concave side of said arc forming said underside of said hollow elongate body head and comprising at its distal end an orifice of diameter sufficient to permit passage of a surgical needle, and said shaft essentially straight; (b) an extendable and retractable support element (54) attached to the distal end of said shaft and disposed such that when said support element is extended, it opposes the underside of said curved hollow elongate body head and is designed to extend such that its distal end will be located along the path of the arc formed by the suture needle; (c) a circular rigid hollow tube (34) adapted to be attached to a needle and to carry a guide wire (130), said rigid circular hollow tube movably disposed at least partially within said hollow body such that said rigid circular hollow tube can move along the proximal-distal direction of said body and through said orifice; (d) a driving mechanism housing (10) attached to the proximal side of said body; (e) a handle (12) attached to at least one of said driving mechanism housing and the underside of said shaft; (f) a support element driving mechanism disposed at least partially within said driving mechanism housing and connected to said support element control and said support element such that upon activation of said support element control, said support element driving mechanism drives the motion of said support element; (g) a hollow tube driving mechanism independent of said support element driving mechanism, adapted to control the motion of said hollow tube, said hollow tube driving mechanism disposed at least partially within said driving mechanism housing; (h) at least one support element control adapted to control the movements of said support element driving mechanism; and (i) at least one hollow tube control adapted to control the movements of said hollow tube driving mechanism. It is within the essence of the invention wherein upon activation of said hollow tube driving mechanism, said hollow tube is moved distally along a generally curved path.

It is within the essence of the invention wherein said hollow tube driving mechanism and said support element driving mechanism are operated independently.

It is further within the essence of the invention wherein said support element, when extended and said hollow elongate body head are adapted to grasp said bone from at least two points along the circumference of the bone.

It is further within the essence of the invention wherein upon activation of said hollow tube driving mechanism, said hollow tube is moved distally along a generally curved path so as to penetrate said bone; further wherein upon activation of said support element, the same is extended and provides support to said needle from the underside of said curved hollow elongate body head, such that said bone is being grasped by said extendable and retractable support element and said hollow elongate body head.

It is a further object of this invention to disclose such a curved/circular bone tunneling device and\or an adjustable suture passer, wherein the extendable and retractable support element is adapted to reach, upon extension, a predetermined location relative to the distal end of said hollow tube, such that the distance between said distal end of said hollow tube and the upper side of said support element provides a slip fit over a bone through which a suture is to be passed.

In other words, the extendable and retractable support, upon extension, is adapted to extend such that its distal end of the same will be located along the path of the arc formed by the suture needle and hollow tube.

It is a further object of this invention to disclose such a curved/circular bone tunneling device and\or an adjustable suture passer, wherein said retractable support element further comprises a needle extractor.

It is a further object of this invention to disclose such a curved/circular bone tunneling device and\or an adjustable suture passer, further comprising a bearing housing disposed between said driving mechanism housing and said shaft.

It is a further object of this invention to disclose a curved/circular bone tunneling device and\or an adjustable suture passer as defined in any of the above, wherein said handle comprises a distally located movable segment and a proximally located stationary segment, said movable segment in physical connection with said support element driving mechanism.

It is a further object of this invention to disclose a curved/circular bone tunneling device and\or an adjustable suture passer as defined in any of the above, wherein said hollow elongate body head (90) further comprises a rigid support element (70) in mechanical communication with said hollow tube (34), adapted to maintain said hollow tube along its path.

It is a further object of this invention to disclose a curved/circular bone tunneling device and\or an adjustable suture passer as defined in any of the above, wherein said hollow elongate body head (90) further comprises a rigid support element (70) that contacts said hollow tube (34) within said hollow elongate body head without impeding its movement in the proximal-distal direction, thereby guiding the movement of said hollow tube and limiting its ability to fold, crimp, or move along a path that diverges from a path from the distal end of said hollow elongate body head to said support element.

It is a further object of this invention to disclose a curved/circular bone tunneling device and\or an adjustable suture passer as defined in any of the above, further incorporating indicating means for indicating the extent of travel, along said arc, of said hollow tube.

It is a further object of this invention to disclose such a curved/circular bone tunneling device and\or an adjustable suture passer, wherein said indicating means comprise a window disposed on one side of said shaft and an indicator located within said shaft, physically connected to said hollow tube driving mechanism such that the distance through which said indicator travels is proportional to the distance the distal end of said hollow tube travels, and disposed such that at least part of the travel of said indicator is visible through said window;

It is a further object of this invention to disclose such the curved/circular bone tunneling device and\or an adjustable suture passer as defined above, further comprising a mark on said side of said shaft in which said window is disposed, said mark disposed such that when said indicator reaches said mark, the distal end of said hollow tube is fully extended.

It is a further object of this invention to disclose the curved/circular bone tunneling device and\or an adjustable suture passer as defined in any of the above, wherein said support element control comprises (a) a threaded rod (24); (b) a rotatable handle (14) with a threaded orifice through which said threaded rod passes; (c) a quick release pin (16) having an engaged configuration and a disengaged configuration, adapted to permit motion of said threaded rod (24) when in said engaged configuration and to prevent motion of said threaded rod (24) when in said disengaged configuration; and (d) a slider comprising: (i) a cylindrical orifice (26) of internal diameter greater than the external diameter of said threaded rod, said cylindrical orifice disposed about said cylindrical rod distally relative to said rotatable handle; (ii) a tab (22) physically connected to said support element driving mechanism, adapted to slide along the proximal-distal axis of said body, and disposed partially within and partially without said body; and (iii) rigid connecting means physically connecting said tab to said cylindrical orifice.

It is a further object of this invention to disclose the curved/circular bone tunneling device and\or an adjustable suture passer as defined in any of the above; wherein said hollow tube control comprises a rotatable handle (18) physically connected to said hollow tube driving mechanism such that the distance through which the distal end of said hollow tube travels is proportional to the rotational angle through which said rotatable handle is rotated.

It is a further object of this invention to disclose such the curved/circular bone tunneling device and\or an adjustable suture passer, wherein said rotatable handle comprises a hollow shaft, said hollow shaft internally threaded and disposed so as to engage a threaded rod physically attached to the proximal end of said hollow tube driving mechanism.

It is a further object of this invention to disclose the curved/circular bone tunneling device and\or an adjustable suture passer as defined in any of the above, wherein said hollow tube control further comprises a hollow tube driving mechanism release tab (20) physically connected to said hollow tube driving mechanism such that activation of said driving mechanism release drives said hollow tube distally to its furthest position.

It is a further object of this invention to disclose the curved/circular bone tunneling device and\or an adjustable suture passer as defined in any of the above, wherein said hollow tube driving mechanism imparts sufficient force to said hollow tube such that a needle attached to the distal end of said hollow tube is provided with sufficient force to penetrate bone.

It is a further object of this invention to disclose the curved/circular bone tunneling device and\or an adjustable suture passer as defined in any of the above, wherein said sufficient force is in the range of about 500 to about 600 Newton. It is a further object of this invention to disclose the curved/circular bone tunneling device and\or an adjustable suture passer as defined in any of the above, wherein said hollow tube driving mechanism comprises (a) at least one track disposed within said hollow elongate body along said body's distal-proximal axis; (b) a connecting wire (132), forming a loop within said hollow elongate body, the proximal end of said loop physically connected to said hollow tube control mechanism; (c) a distal slidable member (4) disposed within said track and adapted to slide along it while allowing said guide wire (130) and one leg of said loop formed by said connecting wire to pass through said hollow elongate body unhindered, said distal slidable member comprising (i) a substantially flat distal edge and (ii) a channel passing through said distal slidable member through which the second leg of said loop formed by said connecting wire passes; (d) a plurality of additional slidable members (2) disposed within said track and adapted to slide along it while allowing said guide wire (130) and one leg of said loop formed by said connecting wire to pass through said hollow elongate body unhindered, each of said additional slidable members comprising a channel passing through said distal slidable member through which the second leg of said loop formed by said connecting wire passes; and (e) a hollow tube actuator (6) disposed within said body proximally to the most proximally located slidable member and disposed so as to engage said hollow tube control.

It is a further object of this invention to disclose a curved/circular bone tunneling device and\or an adjustable suture passer as defined in any of the above, wherein said slidable members (beads) (2,4) have the shape of a cylinder with an indentation (204) about its circumference, said channel (206) passing through said cylinder within indentation substantially perpendicular to the longitudinal axis of said cylinder.

It is a further object of this invention to disclose a curved/circular bone tunneling device and\or an adjustable suture passer as defined in any of the above, wherein said hollow elongate body further comprises at least one body slot (330) along at least part of its length, said hollow elongate body head further comprising at least one hollow elongate body head slot (390) along at least part of its length, and said hollow tube driving mechanism comprises (a) a hollow tube actuator (310) physically connected to said hollow tube control, said hollow tube actuator disposed within said elongate hollow body and adapted to slide along the proximal-distal axis of said hollow body; and (b) a yoke (300) disposed external to said hollow elongate body, said yoke pivotally connected substantially at its proximal end to said hollow tube actuator via a connection that passes through said body slot (330) and at pivotally connected substantially at its distal end to said hollow tube via a connection that passes through said hollow elongate body head slot (390).

It is a further object of this invention to disclose a curved/circular bone tunneling device and\or an adjustable suture passer as defined in any of the above, wherein said support element driving mechanism comprises an actuator (58) disposed along the underside of said hollow elongate body and adapted to slide along the distal-proximal axis of said hollow elongate body and to engage the distal end of said support element control and the proximal end of said support element.

It is a further object of this invention to disclose a curved/circular bone tunneling device and\or an adjustable suture passer as defined in any of the above, wherein said support element driving mechanism comprises (a) an actuator (58) disposed along the underside of said hollow elongate body and adapted to slide along the distal-proximal axis of said hollow elongate body and to engage the distal end of said support element control and the proximal end of said support element; and (b) a yoke (340) pivotally connected at its proximal end to said actuator (58) and pivotally connected to said support element.

It is a further object of this invention to disclose a curved/circular bone tunneling device and\or an adjustable suture passer as defined in any of the above, wherein at least one of said hollow tube control and said support element control is actuated mechanically by a motor.

It is a further object of this invention to disclose a curved/circular bone tunneling device and\or an adjustable suture passer as defined in any of the above, wherein said curved/circular bone tunneling device and\or said adjustable suture passer comprises a tendon holder.

It is a further object of this invention to disclose such a curved/circular bone tunneling device and\or a suture passer, wherein said tendon holder comprises a grasping member (800), disposed on the upper side of said elongate body such that it may slide along the distal-proximal axis of said elongate body between said body and said hollow elongate body head, and which for at least part of its travel the distal end of which extends beyond the distal end of said body; a slider (810) slidably connected to said hollow elongate body, the distal end of which is attached to the proximal end of said grasping member; and a manipulator (820) disposed on the upper side of said elongate body and attached to the proximal side of said slider.

It is a further object of this invention to disclose the curved/circular bone tunneling device and\or a suture passer as defined above, wherein said hollow tube is characterized by having at least one selected from a group consisting of outer diameter in the range of about 1 to about 3 mm; internal diameter (through which the guide wire passes) in the range of about 0.5 to about 1.5 mm; radius of curvature in the range of about 7.5 mm to about 15 mm; or any combination thereof.

It is a further object of this invention to disclose the curved/circular bone tunneling device and\or a suture passer as defined above, wherein said needle is characterized by having cross sectional area selected from a group consisting of circular, triangular, rectangular or any combination thereof.

It is a further object of this invention to disclose the curved/circular bone tunneling device and\or a suture passer as defined above, wherein said rigid circular hollow tube is characterized by having cross sectional area selected from a group consisting of circular, triangular, rectangular or any combination thereof.

It is a further object of this invention to disclose the curved/circular bone tunneling device and\or a suture passer as defined above, wherein said rigid circular hollow tube is made of biocompatible metal selected from hardened corrosion resistant steel.

It is a further object of this invention to disclose a method for tunneling through a bone during arthroscopic surgery, said method comprising: (a) providing a curved bone tunneling device comprising: (i) a hollow elongate body with a hollow elongate body head defining a circular arc; said hollow elongate body head comprising a surgical needle adapted to tunnel through a bone along a path formed by said circular arc; and, (ii) a hollow elongate body comprising an extendable and retractable support element, reconfigurable from at least one extended configuration to at least one retracted configuration; (b) positioning said hollow elongate body of said device adjacent to the circumference of a bone; (c) fixating said needle to said bone; (d) extending said retractable support element to a location along the path formed by said circular arc; thereby grasping said bone with said support element and said hollow elongate body at two points along the circumference of said bone; (e) actuating said needle, thereby tunneling through said bone along said circular arc path; wherein said step of tunneling through said bone is performed without drilling.

It is a further object of this invention to disclose a method for tunneling through a bone during arthroscopic surgery and attaching a tissue, muscle or a ligament to a bone without the use of an anchor, said method comprising: (a) providing a curved bone tunneling device comprising (i) a hollow elongate body having a top side and an underside, comprising a hollow elongate body head (90) and a shaft (50), said hollow elongate body head located at the distal end of said shaft and defining an essentially circular arc with the concave side of said arc forming said underside of said hollow elongate body head; and, comprising at its distal end an orifice of diameter sufficient to permit passage of a surgical needle; (ii) an extendable and retractable support element (54) attached to the distal end of said shaft and disposed such that when said support element is extended, it opposes the underside of said curved hollow elongate body head and located along the path formed by said circular arc; wherein said support element, when extended and said hollow elongate body head are adapted to grasp said bone from at least two points along the circumference of said bone; (iii) a rigid hollow tube (34) adapted to be reversibly attached to a needle and to carry at least one guide wire (130), said hollow tube movably disposed at least partially within said hollow body such that said rigid hollow tube can move along the proximal-distal direction of said body and through said orifice in said hollow elongate body head; (iv) a support element driving mechanism, adapted, upon activation of a support element control, to drive the motion of said support element; (v) a rigid hollow tube driving mechanism independent of said support element driving mechanism, adapted to control the motion of said hollow tube; (b) passing a guide wire through a device capable of imparting sufficient force to a surgical needle such that the surgical needle will pass through bone; (c) attaching a surgical needle to said guide wire; (d) attaching a suture to the proximal end of said guide wire; (e) connecting said surgical needle to said hollow elongate body; (f) positioning said hollow elongate body head of said device adjacent to the circumference of a bone; (g) extending said retractable support element to the underside of said curved hollow elongate body head at a location along the path formed by said circular arc; thereby grasping said bone with said support element and said hollow elongate body head at two points along the circumference of said bone; (h) actuating said rigid hollow tube and said needle, thereby tunneling said needle through said bone; and, (i) pulling said guide wire through said bone, thereby pulling said suture through said soft tissue and attaching said soft tissue to said bone. actuating said needle, thereby passing said needle through said bone; and pulling said guide wire through said bone, thereby pulling said suture through said soft tissue and attaching said soft tissue to said bone.

It is a further object of this invention to disclose such a method, wherein said surgical needle is a rigid surgical needle.

It is a further object of this invention to disclose such a method, wherein said surgical needle is a rigid and either straight or has a substantially circular/curved shape.

It is a further object of this invention to disclose such a method, wherein said rigid circular hollow tube is sufficiently rigid so that its circular shape is maintained as it penetrates said bone along said circular arc.

It is a further object of this invention to disclose such a method, wherein said step of tunneling through said bone additionally comprises the step of, tunneling said needle along said circular arc path.

It is a further object of this invention to disclose such a method, additionally comprising a step of maintaining said needle within said device.

It is a further object of this invention to disclose such a method, wherein said step of extending said a support element further comprises step of firmly grasping said bone along a circumference of said bone.

It is a further object of this invention to disclose such a method, said step of actuating said hollow tube additionally comprising step of distally moving said rigid hollow tube along a generally curved path so as to penetrate said bone.

It is a further object of this invention to disclose such a method, wherein upon activation of said support element, the same is extended and fixate the position of said hollow elongate body head (90) and said needle so as to ensure the same remain flush with said bone surface.

It is a further object of this invention to disclose such a method, wherein upon activation of said support element, the same is extended and fixate said needle from the underside of said curved hollow elongate body head, such that when said support element is extended, the same is located along the path of the arc formed by the suture needle so as to grasp said bone by said extendable and retractable support element and said hollow elongate body head.

It is a further object of this invention to disclose such a method, wherein upon activation of said support element, the same is extended and provides support to said needle from the underside of said curved hollow elongate body head, such that when said support element is extended, the same is located along the path of the arc formed by the suture needle so as to grasp said bone by said extendable and retractable support element and said hollow elongate body head.

It is a further object of this invention to disclose such a method, wherein said hollow tube driving mechanism and said a support element driving mechanism are operated independently.

It is a further object of this invention to disclose such a method, wherein the extendable and retractable support element is adapted to reach, upon extension, a predetermined location relative to the distal end of said hollow tube, such that the distance between said distal end of said hollow tube and the upper side of said support element provides a slip fit over a bone through which a suture is to be passed.

In other words, the extendable and retractable support, upon extension, is designed to extend such that its distal end of the same will be located along the path of the arc formed by the suture needle.

It is a further object of this invention to disclose such a method, wherein said extendable and retractable support element further comprises a needle extractor (60).

It is a further object of this invention to disclose such a method, additionally comprising step of controlling the movements of said support element driving mechanism.

It is a further object of this invention to disclose such a method, additionally comprising step of controlling the movements of said rigid hollow tube driving mechanism.

It is a further object of this invention to disclose such a method, additionally comprising step of performing said arthroscopic surgery without the need of drilling through said bone or removing of bone material.

It is a further object of this invention to disclose such a method, additionally comprising step of incorporating indicating means for indicating the extent of travel of said hollow tube.

It is a further object of this invention to disclose such a method, wherein said indicating means comprise (a) a window disposed on one side of said shaft; and, (b) an indicator located within said shaft, physically connected to said rigid hollow tube driving mechanism such that the distance through which said indicator travels is proportional to the distance the distal end of said rigid hollow tube travels, and disposed such that at least part of the travel of said indicator is visible through said window.

It is a further object of this invention to disclose such a method, further comprising a mark on said side of said shaft in which said window is disposed, said mark disposed such that when said indicator reaches said mark, the distal end of said rigid hollow tube is fully extended.

It is a further object of this invention to disclose such a method, wherein said sufficient force is in the range of about 500 to about 600 Newton.

It is a further object of this invention to disclose such a method, additionally comprising step of providing said hollow tube having at least one property selected from a group selected from outer diameter in the range of about 1 to about 3 mm; internal diameter in the range of about 0.5 to about 1.5 mm; radius of curvature in the range of about 7.5 mm to about 15 mm; or any combination thereof.

It is a further object of this invention to disclose such a method, additionally comprising step of providing said needle with cross sectional area selected from a group consisting of circular, triangular, rectangular or any combination thereof.

It is a further object of this invention to disclose such a method, additionally comprising step of providing said rigid circular hollow tube being characterized by having a cross sectional area selected from a group consisting of circular, triangular, rectangular or any combination thereof.

It is a further object of this invention to disclose such a method, additionally comprising step of providing said rigid circular hollow tube made of biocompatible metal selected from hardened corrosion resistant steel.

BRIEF DESCRIPTION OF THE DRAWINGS

The invention disclosed herein is now described with reference to the drawings, wherein:

FIG. 9 presents isometric views of the support element control according to a preferred embodiment of the invention;

DETAILED DESCRIPTION OF THE PREFERRED EMBODIMENTS

Figure 1A:
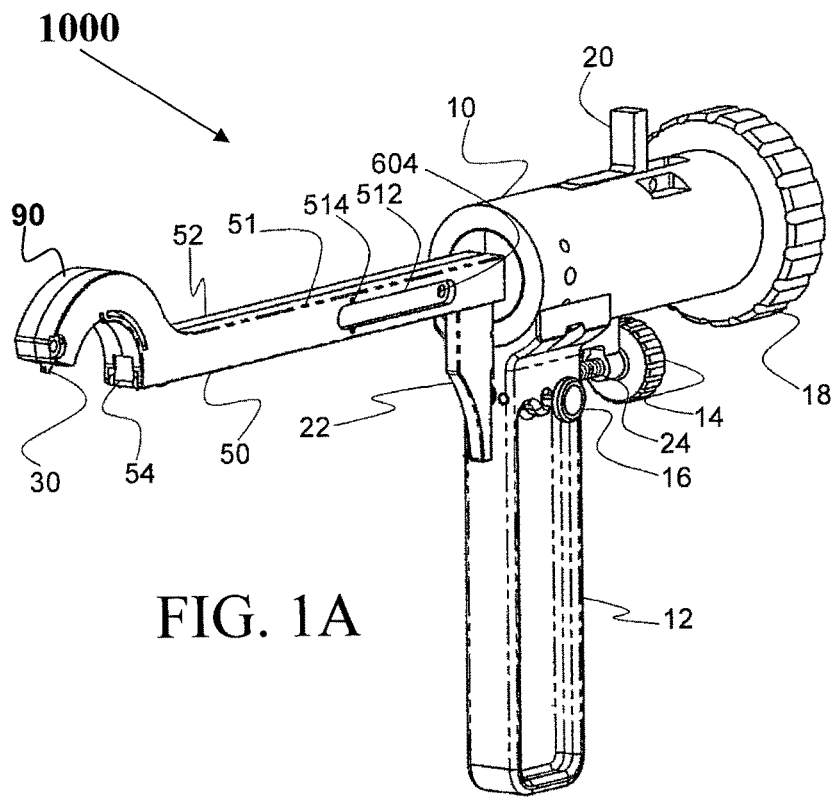
FIG. 1 presents isometric drawings of the curved/circular bone tunneling device or adjustable suture passer herein disclosed according to one embodiment of the invention.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The present invention provides a circular bone tunneling device, for use in arthroscopic surgery, comprising:

a. a hollow elongate body comprising a hollow elongate body head defining a rigid circular arc; said hollow elongate body head comprising a surgical needle adapted to tunnel through a bone along a path formed by said circular arc; and, b. an extendable and retractable support element, reconfigurable from at least one extended configuration to at least one retracted configuration.

It is within the cores essence of the present invention where said support element, in said extended configuration, is adapted to be located along said path formed by said circular arc.

It is within the core essence of the present invention where said support element, in said extended configuration, and said hollow elongate body are adapted to grasp said bone from at least two points along the circumference of said bone.

According to another embodiment of the present invention the surgical needle as defined above, is a rigid surgical needle.

According to another embodiment of the present invention the surgical needle's shape is slightly curved and approximately defines a circular arc.

The present invention also provides a method for tunneling through a bone during arthroscopic surgery. The method comprising steps of (a) providing a curved bone tunneling device comprising a hollow elongate body comprising, a hollow elongated body head (refers hereinafter as head); said head defining a circular arc; said hollow elongate body comprising a surgical needle adapted to tunnel through a bone along a path formed by said rigid circular arc; and, an extendable and retractable support element, reconfigurable from at least one extended configuration to at least one retracted configuration; (b) positioning said hollow elongate body of said device adjacent to the circumference of a bone; (c) fixating said needle to said bone; (d) extending said retractable support element to a location along the path formed by said rigid circular arc; thereby grasping said bone with said support element and said hollow elongate body at two points along the circumference of said bone; (e) actuating said rigid hollow tube and said needle, thereby tunneling through said bone along said rigid circular arc path; wherein said step of tunneling through said bone is performed without any drilling.

As described above, the present invention provides an arthroscopic bone tunneling device which tunnels through an arc defined by two points on the circumference of a bone. The tunnel is formed by penetration of a needle device attached to a rigid hollow tube without the need to drill.

According to one embodiment, the arthroscopic bone tunneling device is connected to a suture which is simultaneously passed through the tunnel so formed. The suture can then be used to fix a, tissue, muscle or ligament to a bone tissue.

The arthroscopic bone tunneling device comprises, inter alia, a rigid hollow tube and which penetrates the bone at a first point along the circumference of the same; and an extendable and retractable support element (will be disclosed hereinafter) which provides counter force at a second point along the circumference of the bone close to where the arc (i.e., the needle) exits the bone. Such an extendable and retractable support element enables the tunneling without drilling.

No anchors are required since the sutures are fixed to through the arc formed in the bone in a full loop configuration.

The extendable and retractable support (which provides the contra) device fixates the bone tunneling device onto the bone while tunneling is being performed.

The entire unit has a low profile when entering the incision and a slightly larger profile when the fixation device is deployed.

Thus the unit is the first truly minimally invasive tool for rotary cuff repair and does not require a large access incision and/or large sub-dermal space to deploy its streamline no drilling configuration.

The circular tunneler/adjustable suture passer of the present invention is characterized by the following advantages:

(a) unlike most of the prior ah devices, the circular tunneler/adjustable suture passer of the present invention performs no drilling through the bone; alternatively the present invention tunnels through the bone by applying consistent and sufficient force to a needle enabled by the force applied on the bone by the retractable support element as counter force to the force applied to the bone by the needle.

(b) the penetration through the bone is performed according to an arc shaped path (e.g. single bone entrance). Several known prior art publications refer to the drilling of two orthogonal bores/channels so as to perform the arthroscopic surgery. As mentioned above, such orthogonal bores are likely to cause fractures to the bone by weakening the same.

(c) the suture passer is adjustable. Due to the novel configuration of the device (namely, the extendable and retractable support element, as will be disclosed hereinafter), the same can accommodate different bone diameters and different shapes and structures. In other words, the device of the present invention is adapted to various sizes, shapes and bone dimensions. The term "about" refers hereinafter to a range of 25% below or above the referred value.

As used herein, the term "needle" is understood to indicate any sharp instrument used in medical practice to penetrate tissue. Thus, as non-limiting examples, the term is understood to include such instruments as surgical needles and lances. It is also understood to include both hollow and solid instruments.

As used herein, the term "slip fit" refers to the mating of two mechanical components.

As used herein the term "ejecting" refers to an act of penetration or tunneling of an element through the bone without any drilling or removing bone material (e.g. debris).

As used herein the term "adjustable" refers to the ability of the circular bone tunneling device/suture passer to accommodate different bone diameters and different shapes and structures.

As used herein the term "support" refers to maintaining the hollow elongate body head unit flush with bone surface by means of fixation of the unit to the bone circumference.

As used herein the term "fixation" refers to non-displacement of the hollow elongate body head and/or the surgical needle and/or the hollow tube when forces are being applied by the hollow tube driving mechanism and insures that the position of the hollow elongate body head and/or the surgical needle and/or the hollow tube are maintained in the same selected position.

Figure 1B:
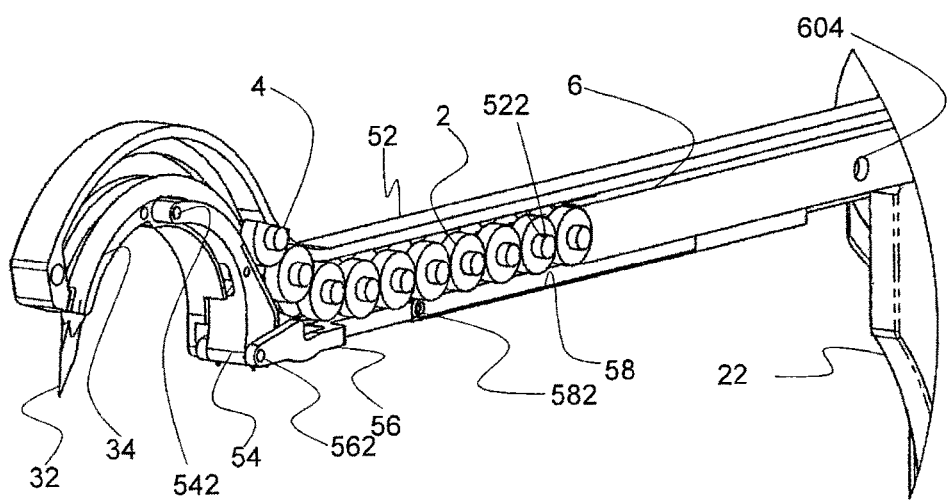
Figure 1C:
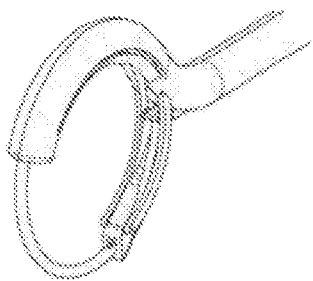

Reference is now made to FIG. 1, which presents isometric drawings of a preferred embodiment 1000 of the invention herein disclosed. FIG. 1A presents an external view of the circular bone tunneling device/adjustable suture passer. A hollow elongate body forms the distal portion of the tool. The distal portion of the body comprises a hollow elongate body head 90 (refers hereinafter as head or hollow elongate body head), which is curved downwards; as shown in the illustration, in preferred embodiments, the head describes a rigid and an essentially semicircular arc, the concave side of the arc being on the underside. The proximal portion is a shaft 50. In preferred embodiments of the invention, for ease of assembly the hollow elongate body is made from two separate pieces 51 and 52 which are joined together in the final step of the assembly of the body and the components that are found within. The body may be constructed of any suitable biocompatible material such as a hard inert polymer or metal. The distal end of the head contains an orifice through which a rigid circular hollow tube 34 passes. The rigid circular hollow tube comprises at its distal end a mechanism 30 by which connection can be made with an appropriately-sized surgical needle or lance 32, and is disposed within the head such that it can move back and forth and extend a sufficient distance from the end of the head such that the needle or lance can describe an essentially circular path through a circle of diameter equal to that of the arc described by the head. Means by which a surgical needle or lance can be attached to the end of the rigid circular hollow tube are well-known in the art.

In order to stabilize the bone during extension of the needle so that the needle can enter the bone as it is protrudes from the tool, the tool further comprises an extendable and retractable support element 54 that, when extended, will grasp the bone on a second point along the circumference of the bone, other that of the needle. The details of the mechanism by which the support element is activated are given below.

The driving mechanism of the tool is housed within driving mechanism housing 10 attached to the proximal end of the body. The control and mechanisms are located within the driving mechanism housing. A handle 12 is attached to the underside of the tool, either to the body or to the driving mechanism housing or to both. The movements of the hollow tool and the support element are controlled by independent control and driving systems. In the view shown in FIG. 1A, some of the elements of these control and driving systems are visible. Rotatable handle 18 is connected to the driving mechanism for the rigid circular hollow tube such that the motion of the distal end of the rigid circular hollow tube is proportional to the angle through which the handle is turned. Activation of quick-release tab 20 causes the rigid circular hollow tube to move directly to the end of its travel. Also visible in FIG. 1A are some of the components of the support element driving system. Rotatable knob 14 is connected to the driving mechanism of the support element such that the degree to which it is extended is proportional to the angle through which the knob is turned. Rotatable knob 18 comprises a central threaded orifice that engages threaded rod 24; as the knob is turned, it moves down the length of the threaded rod. The control mechanism also includes tab 22 which physically engages the driving mechanism for the support element. The tab includes an orifice that fits over the threaded rod distally to knob 14 and a stiff connector that connects the orifice to the distal end of the tab. The support element control mechanism also includes a quick-release pin 16, activation of which enables the support element to move directly to the end of its travel.

In preferred embodiments of the invention, it also includes means for determining how far the rigid circular hollow tube has traveled. In the embodiment illustrated in FIG. 1A, one side of the shaft includes a window 512. The rigid circular hollow tube driving mechanism includes a mark or other indicator 604 that is visible through the window and indicates the current position of the rigid circular hollow tube relative to the bounds of its travel. A mark 514 is placed on the body; when indicator 604 reaches mark 514, the user knows that the rigid circular hollow tube has reached the end of the travel.

Reference is now made to FIG. 1B, which provides an isometric view of embodiment 1000 after the left-hand side of the body 51 has been removed to reveal the interior of the hollow body. In this embodiment, the driving mechanism for the rigid circular hollow tube comprises a series of slidable members (beads) attached to one another. The interior of the body includes on its upper or lower side or both a track 522 that guides the movement of the slidable members. The distal slidable member 4 is flat on its forward side, which engages the proximal end of the hollow tube. The remaining slidable members 2 need not be flat on the forward side; as described in detail below, in preferred embodiments, they present a substantially circular profile. In this embodiment, the driving mechanism also includes at its proximal end rigid circular hollow tube actuator 6 that engages the rigid circular hollow tube control such that when the rigid circular hollow tube control moves forward, it causes the activator to move forward, thereby causing the slidable members to slide distally, pushing the hollow tube.

Also visible in the view shown in FIG. 1B is the activating mechanism for the support element. In this embodiment, the support element activating mechanism comprises an actuator 58 that engages at its proximal end the distal end of the support element control, and at its distal end support element connecting yoke 56 whereby forward movement of the support element control forces forward movement of actuator 58 (along axis 582) and hence forward movement of connecting yoke 56. The connecting yoke is pivotally connected to the support element via pivot element (e.g. a pin around which the assembly can rotate) 562. When activated, the support element moves along axis 542. It should be emphasized that the distal end of the support element, when activated, is located along the path formed by the rigid circular arc.

According to another embodiment, a circular cross section/profile of the shaft is provided. According to this embodiment, the circular profile ensures the best adhering/joining of the two parts of the incision (through which the circular tunneler/suture passer is being inserted). Such profile significantly reduces any leakage (of e.g. saline, which is typically used by surgeons to expand the inner volume) that may be developed during the operation.

The rigid circular hollow tube driving mechanism described above can provide a force of several hundred Newtons (especially, in the range of about 500 to about 600 Newton) to the hollow tube, which is more than sufficient for the rigid circular hollow tube to penetrate bone.

Figure 2A:
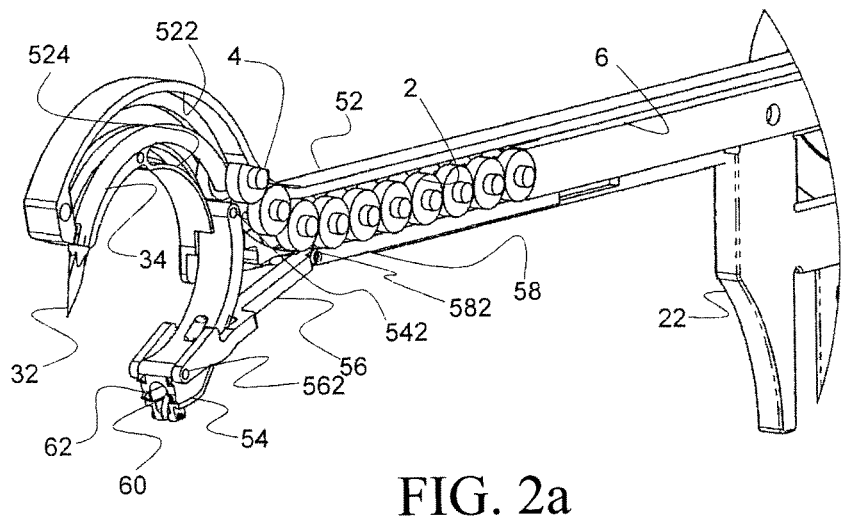
FIGS. 2a-2d presents a view of the curved/circular bone tunneling device or adjustable suture passer herein disclosed in which the support element has been extended.
Figure 2B:
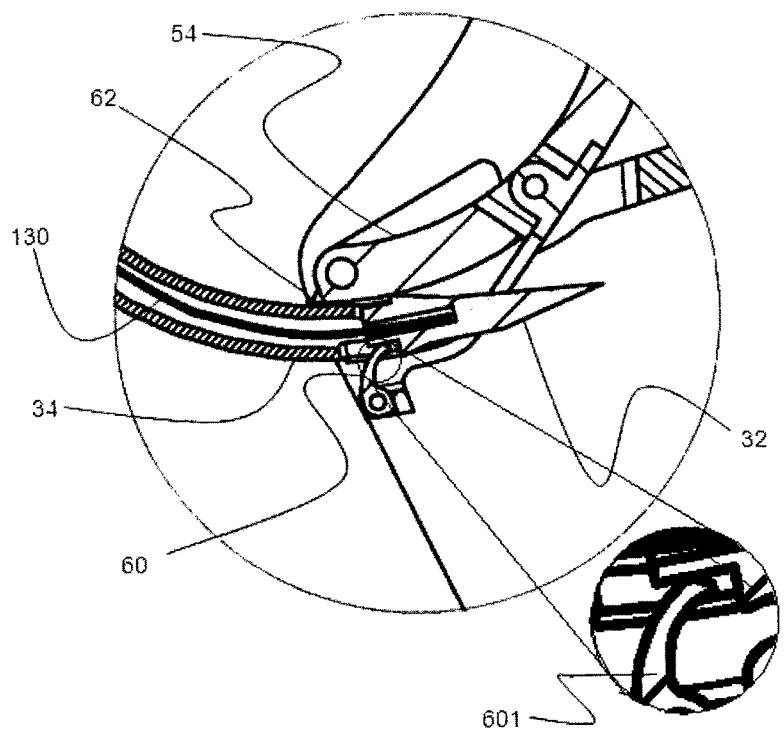

In order to insure that the protruding needle actually penetrates the bone rather than displacing the hollow elongate body head away from the bone surface, support must be provided to maintain the hollow elongate body head unit flush with bone surface by means of fixation of the unit to the bone circumference opposite to the side through which the needle enters. Hence, the tool comprises an extendable/retractable support element which, when extracted, extends from the underside of the tool opposite to the head. Reference is now made to FIGS. 2a and 2b, which shows embodiment 1000 of the tool after the support element 54 has been extended. In preferred embodiments of the invention, the support element additionally comprises a needle extractor 60.

The needle extractor 60 is responsible for maintaining penetrating element 32 within the support element 54. The same is enabled by means of a bore 601 located within the penetrating element 32, into which the needle extractor 60 penetrates so as to prevent the departure of penetrating element 32 from the support element 54.

Penetrating element 32 is a sharp element that can be pushed into the bone and penetrate through it. Penetrating element 32 pulls wire 130 with it (130 is connected to the proximal end of 60).

Once a full arc path from circumference point 1 to circumference point 2 through the bone has been formed, needle extractor 60 remains within the bore 601 [while the arched rigid hollow tube 34 returns back to housing 90.

Needle extractor 60 enables the penetrating element 32 to enter into support element 54 yet, ensures its release from the rigid circular hollow tube 34 when the same moved reversibly back into head.

Needle extractor 60 is an elastic element, bendable in one direction yet stiff in the opposite direction. Embodiment 1000 (illustrated in FIG. 1) discloses needle extractor 60 as a rigid hook rotating on an axis with a torsion spring pushing it.

However, it should be understood that several other embodiments may be utilized. For example, the mechanical properties of the needle extractor 60 (namely, its elasticity and spring-like properties) can be exploited.

Figure 2C:
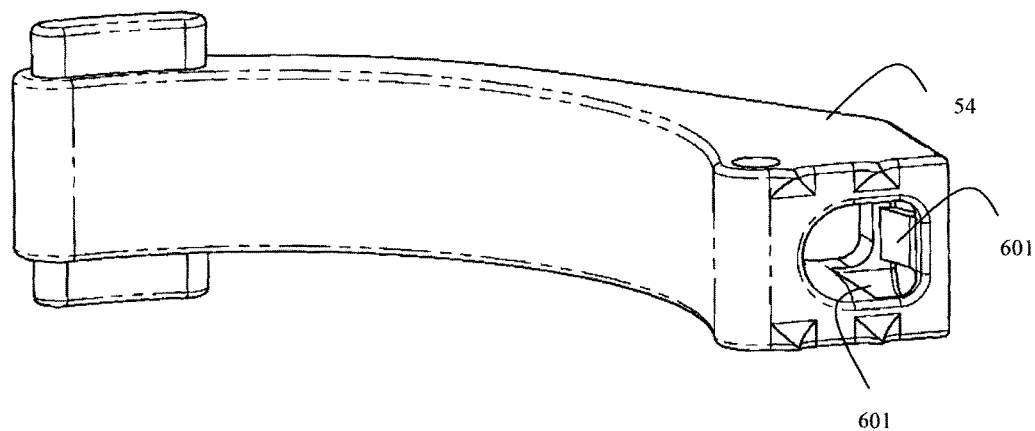
Figure 2D:
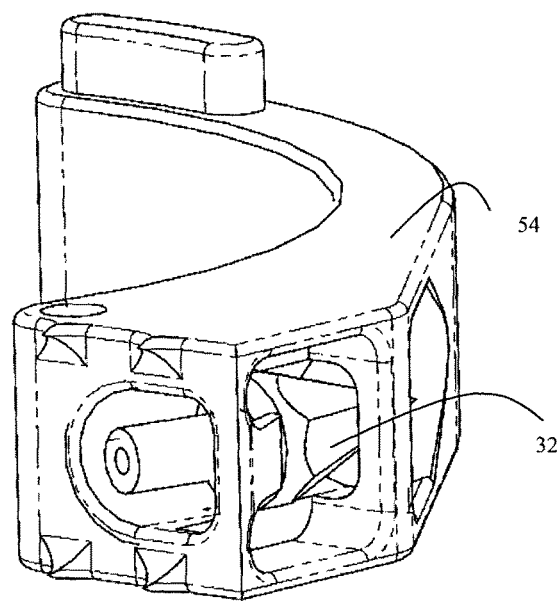

Reference is now made to FIGS. 2c and 2d which illustrates an embodiment in which the spring-like properties of the needle extractor 60 is utilized.

In such an embodiment, the needle extractor 60 may be integrated into support element's 54 internal surface. According to this embodiment, the needle extractor 60 is characterized by two configurations, an extended configuration and a retracted configuration.

In the extended configuration, the needle extractor 60 substantially reduces the support element's 54 inner diameter; and, in the retracted configuration of the needle extractor 60, the support element's 54 inner diameter remains substantially the same.

Due to the needle extractor's 60 spring-like properties, it can be reconfigured from the extracted configuration to the retracted configuration by application of force on the same. Once no force is applied, the needle extractor 60 is reconfigured back from the retracted configuration to the extended configuration.

The default configuration of the needle extractor 60, according to this embodiment is the extended configuration, in which the inner diameter of support element 54 is reduced.

Once, the penetrating element 32 enters the support element 54, the needle extractor 60 is reconfigured from the extended configuration to the retracted configuration and applies pressure on the penetrating element 32, \so as to maintain the same within support element 54.

It should be emphasized that the support element 54 may comprise either one or a plurality of said needle extractor 60.

Reference is now made to FIG. 2d which illustrates the above mentioned embodiment, but with the penetrating element 32 integrated within the support element 54.

FIG. 2b illustrates a close up view of how the needle extractor 60 functions once penetrating element (e.g., needle or lance) 32 are within the support element 54 and after the rigid circular hollow tube 34 is withdrawn back.

It should be noted that the distal face of element 54 is equipped with prongs 62, adapted to prevent any movement of the support element 54, once the same is positioned at desired location.

In preferred embodiments, the needle extractor is disposed on the underside of the support element and comprises a hollow receptacle into which the penetrating element (needle or lance) 32 enters upon reaching circumference point 2.

When either the support element or the rigid circular hollow tube is retracted following use of the tool, the penetrating element remains within hollow receptacle of the needle extractor 60.

Figures 3, 4:
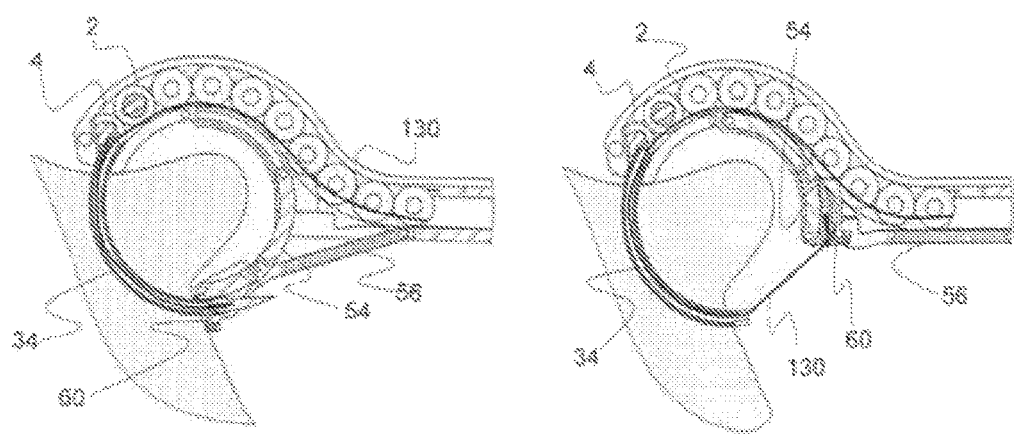
FIG. 3 presents a cross-sectional view of the distal end of the curved/circular bone tunneling device or adjustable suture passer herein disclosed illustrating its use to insert a guide wire through a bone.
FIG. 4 presents the same view as in FIG. 3, but after the support element has been retracted.

Reference is now made to FIG. 3, which shows a cross-sectional view of embodiment 1000 of the tool after the rigid circular hollow tube has completed its travel. A guide wire 130 passes through the rigid circular hollow tube and is attached to the proximal end of the lance 32 (which in this view has passed through the bone, shown as a shaded region in the figure).

A suture can then be attached to the distal end of the guide wire and passed through the soft tissue and into and through the bone. In the view shown in FIG. 3, the needle has entered into the needle extractor 60.

Reference is now made to FIG. 4, which shows a cross-sectional view of the tool after the support element has been retracted. In this view, the rigid circular hollow tube is still within the bone, and needle can be seen to have remained within the needle extractor, carrying guide wire 130 with it.

A cavity in retractable support element 54 provides a 'nesting volume' for the penetrating element 32 securing it to its position, so as to prevent any damage to surrounding tissues.

Reference is now made to FIGS. 5A-5D, which illustrate the distal end of another preferred embodiment of the tool. According to this embodiment, an additional radial support is provided to rigid circular hollow tube 34 sections that aren't yet within the bone in order to ensure that at the end of its travel it will engage needle extractor 60.

In this embodiment, the support element further comprises a tab 5421 that protrudes through a slot 5422 in one side of the head (90).

Tab 5421 slides in a slot 5422 so as to indicate the current position of the rigid circular hollow tube relative to the bounds of its travel.

Most significantly, this embodiment further includes rigid support element 70. The support element is located between the right and left halves of the head; in a preferred embodiment of the device, the head and body are manufactured from two matching pieces that form the left and right halves of the device when it has been assembled.

Figure 5A:
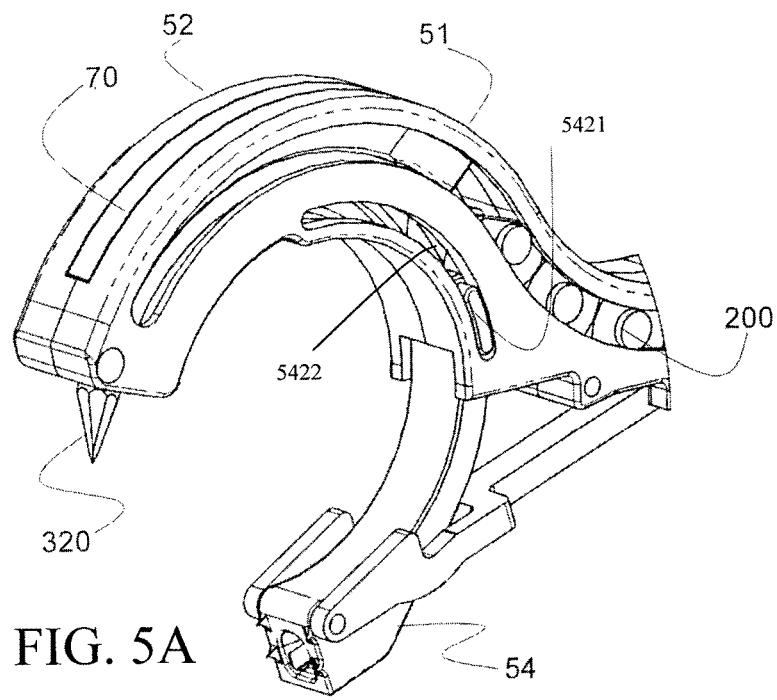
FIG. 5 presents views of the distal end of another preferred embodiment of the invention.

FIG. 5A shows an external view of head 90, including rigid support element 70. The same illustrating how it sits between the two halves of the head.

Figure 5B:
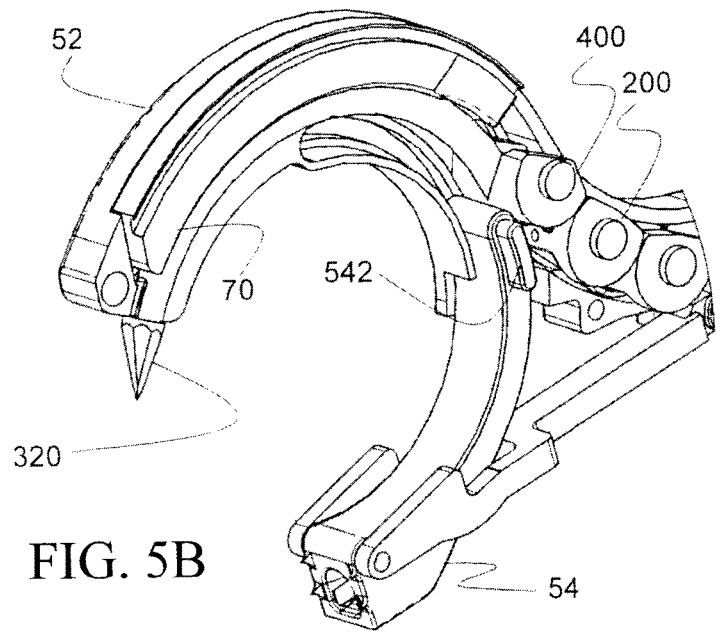
Figure 5C:
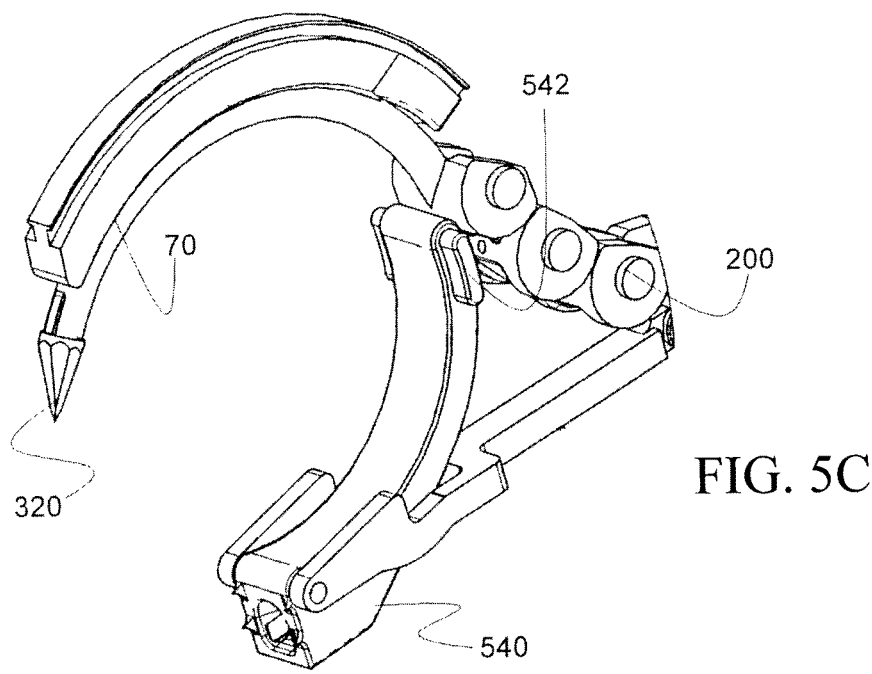
Figure 5D:
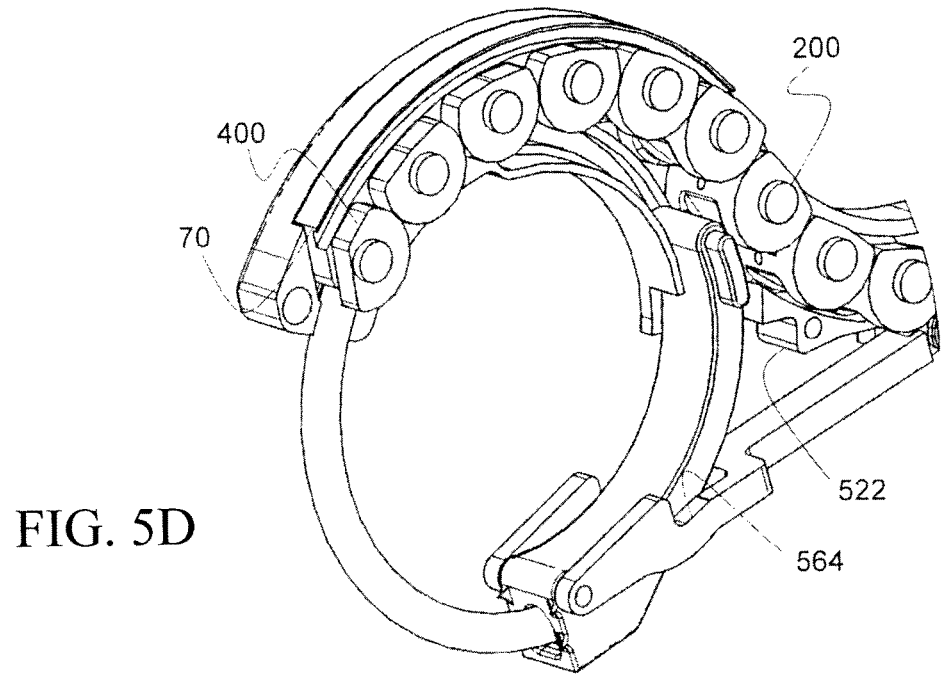

FIG. 5B shows a partial cutaway view of the head with support element 70 in place. An isometric view of rigid support element 70 can be seen in FIG. 5C. Support element 70 has the shape of an arc with essentially the same curvature as the upper portion of head 90. Slots on either side of the support element hold it in place between the two halves of the head when it is assembled. Support element 70 has a depth sufficient to contact rigid circular hollow tube 34 while not hindering the movement of the hollow tube. Rigid support element thus provides additional support to rigid circular hollow tube 34 and prevents it from bending or crimping (and any other deformation) such that the rigid circular hollow tube is constrained to move only along a path that will return it to needle catcher 60, as shown in FIG. 5D and FIG. 6D

Figure 6A:
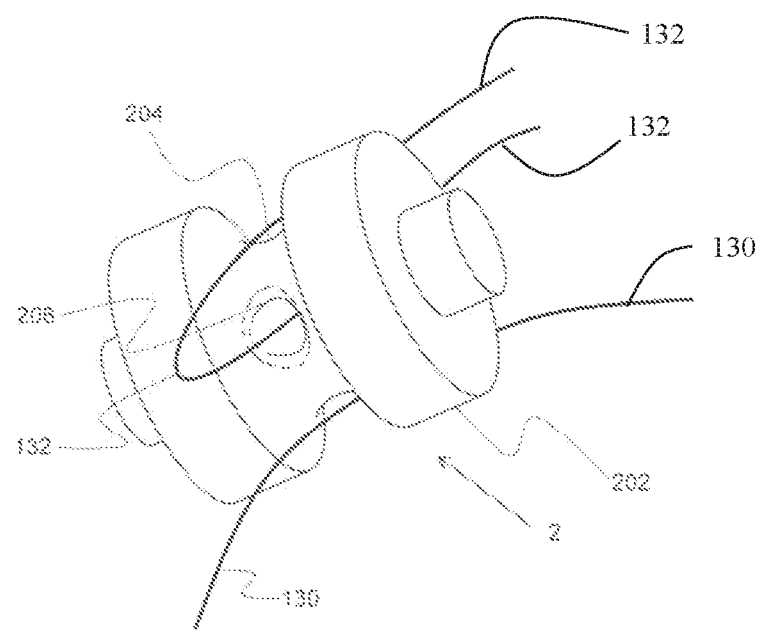
FIG. 6 presents illustrations of slidable members 2 and 4 according to a preferred embodiment of the invention.

Reference is now made to FIG. 6A, which illustrates a preferred embodiment of slidable member 2. In preferred embodiments, the slidable member is substantially cylindrical in shape, with an indentation 204 around the waist of the cylinder (i.e. around its circumference and perpendicular to the cylinder's longitudinal axis). The indentation allows guide wire 130 to pass unhindered. At least one of the ends 202 fits into track 522 that enables the member to slide along the distal-proximal axis of the body. Note that even though the member has a circular cross-section, it does not roll along the track.

A channel 206 passes through the slidable member along an axis substantially perpendicular to the longitudinal axis of the cylinder. A connecting wire 132, disposed along the proximal-distal axis of the body, passes through the channel, thereby connecting the plurality of slidable members. The connecting wire is formed into a loop, the proximal end of which engages the rigid circular hollow tube driving mechanism, enabling the rigid circular hollow tube to be retracted after the tool has been used. As shown in the figure, as with guide wire 130 the leg of the loop in connecting wire 132 that does not pass through the channel passes outside the slidable member via indentation 204.

Figure 6B:
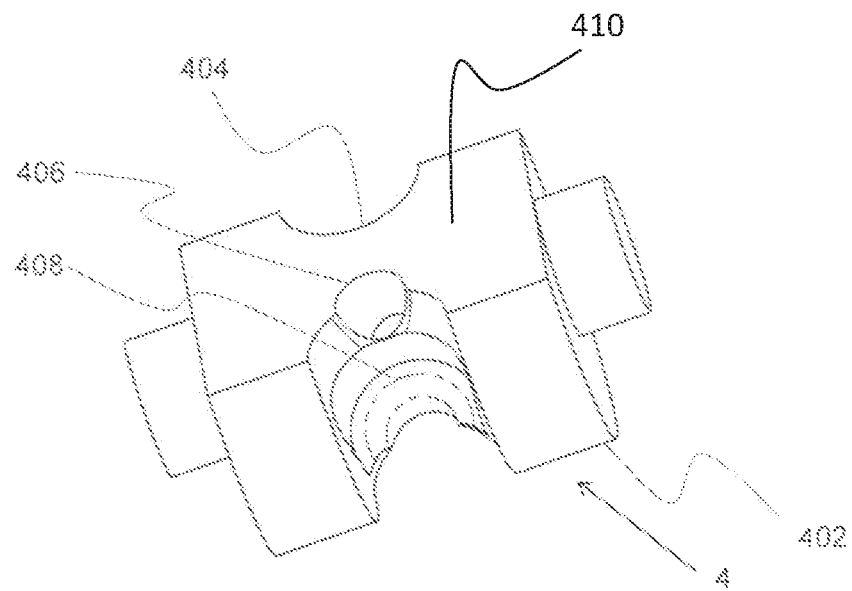

Reference is now made to FIG. 6B, which illustrates a preferred embodiment of distal slidable member 4. The overall cylindrical shape 402, indentation 404, and channel 406 are analogous to components 202, 204, and 206 of slidable member 2 illustrated in FIG. 5A. Unlike the other slidable members, the distal slidable member directly engages/actuates rigid circular hollow tube 34. Thus, it is provided with a flat face 410 that is oriented facing forward (i.e. in the direction of motion toward head 90), and a channel 408 that fits over the proximal end of rigid Circular hollow tube 34 and, in preferred embodiment, is physically connected thereto.

Figure 6C:
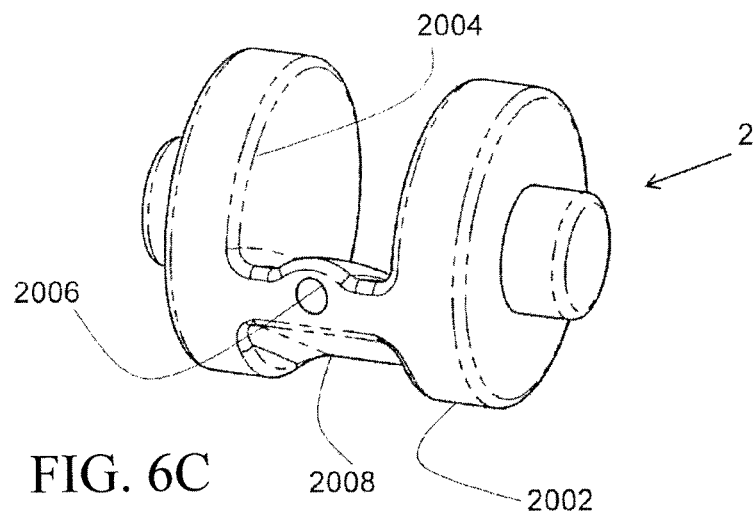
Figure 6D:
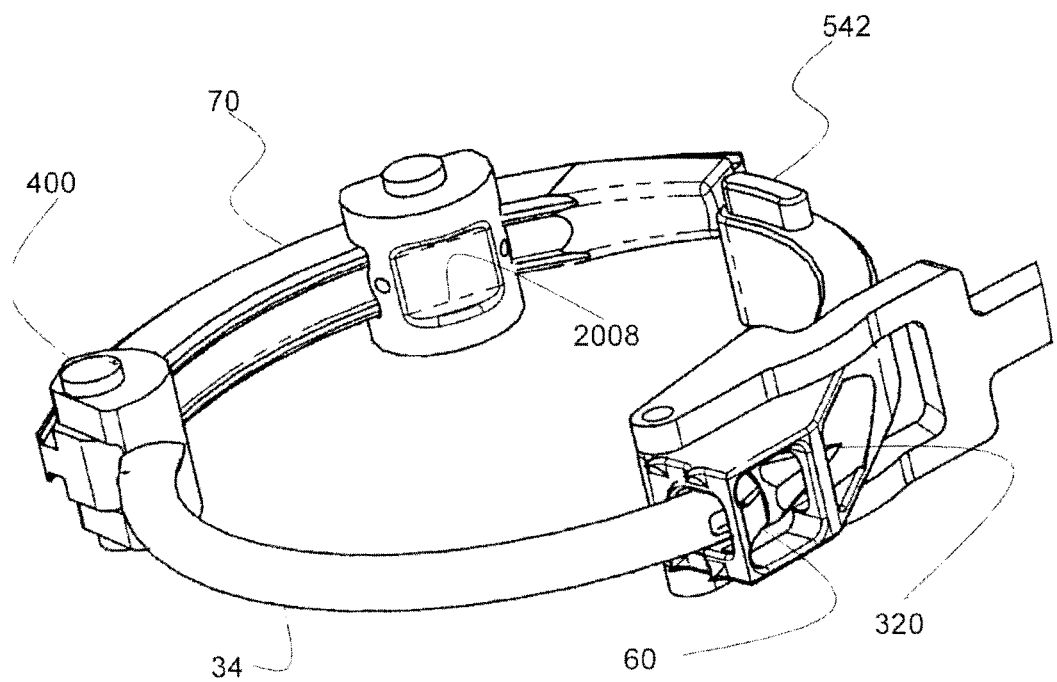

In embodiments of the invention that incorporate rigid support member 70, slidable members 2 have a somewhat different configuration from that shown in FIG. 6A. The configuration of slidable member 2 in these embodiments is shown in FIG. 6C. While the slidable member retains its generally cylindrical shape, the indentation is no longer symmetrical about the axis of the cylinder. Rather, indentation 2004 is cut through most of the diameter of the cylinder so that the slidable member 2 may pass under support element 70. Consequently, channel 2006 adapted to allow passage of connecting wire 132 is displaced from the center, as shown in the diagram. A second indentation 2008 is made on the opposite side of the member to allow passage of guide wire 130. One side of the cylinder (2002) is adapted to slide on track 522. A schematic assembly diagram showing support member 70, slidable member 2, and rigid circular hollow tube 34 in its extended position (i.e. after the needle attached to it has reached needle catcher 60), is given in FIG. 6D.

Figure 7:
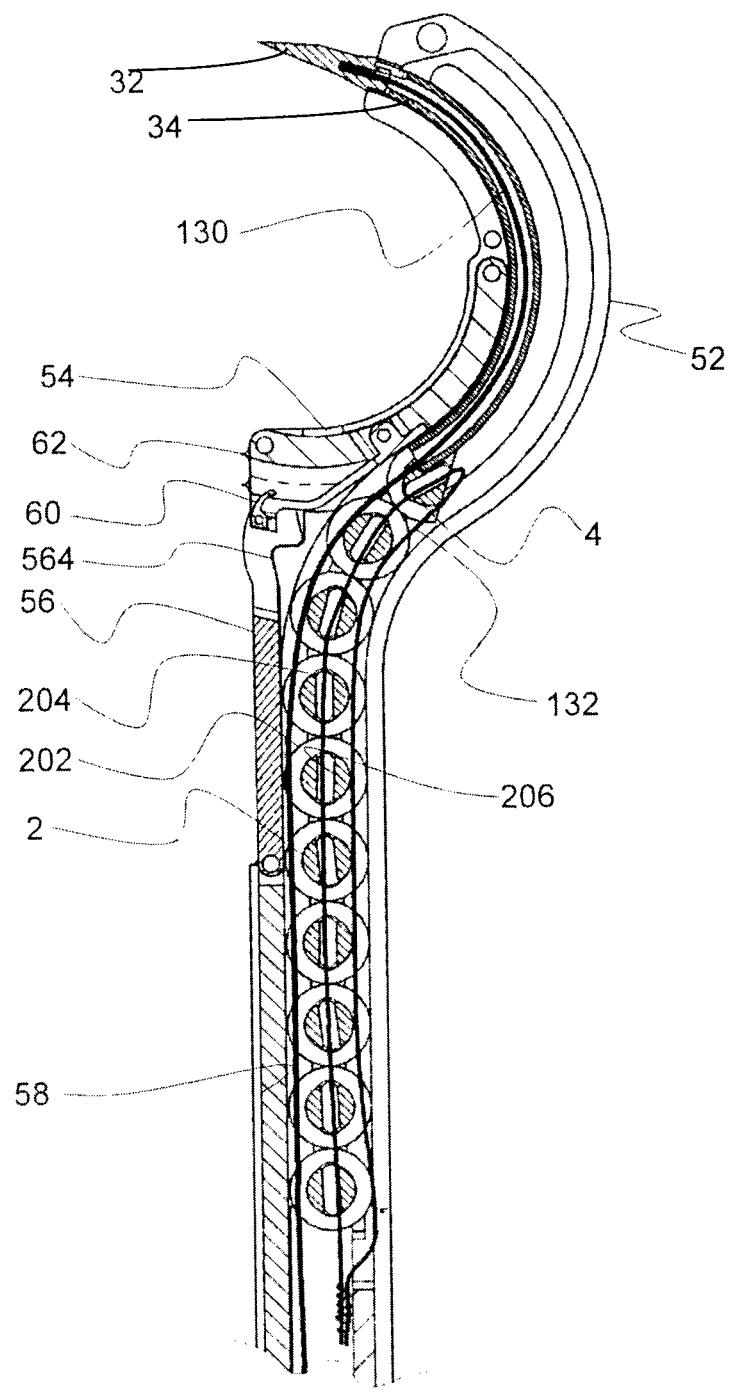
FIG. 7 presents a cross-sectional view of the assembly of the rigid hollow tube driving mechanism according to a preferred embodiment of the invention.

Reference is now made to FIG. 7, which, presents a cross-sectional view of the assembly of the rigid circular hollow tube driving mechanism according to one embodiment of the invention. The slidable members are connected via connecting wire 132 through orifices 206 and 406 to form a train. Connecting wire 132 loops back through indentations 204 and 404; the proximal end of the loop engages the rigid circular hollow tube control such that when the rigid circular hollow tube control is activated, the slidable members move in tandem, thereby moving the rigid circular hollow tube 34 and the needle or lance 32 connected to its distal end. Guide wire 130 passes through indentations 204 and 404, whereby motion of the guide wire, which as described above passes through the rigid circular hollow tube 34 and is connected to needle or lance 32, is unimpeded.

Reference is now made to FIG. 8, which presents isometric views of the hollow tube (driving mechanism) control according to a preferred embodiment of the invention.

The control mechanism is disposed within and about driving mechanism housing 10. Rotatable knob 18 comprises a substantially circular handle (in preferred embodiments, it is knurled or its circumference is provided with a plurality of indentations or protrusions for ease of handling) and a hollow shaft 186 the internal wall of which is threaded. Driving mechanism housing 10 comprises a channel of internal diameter appropriate to provide a slit fit to hollow shaft 186 and a distal wall with an orifice through which hollow tube actuator 6 passes. The threaded shaft further comprises a groove 182 around the circumference of its external wall, substantially perpendicular to the longitudinal axis of the shaft, and disposed substantially at its distal end. The threaded hollow shaft engages a threaded rod 602 which is physically connected to the proximal end of hollow tube actuator 6. A hollow tube driving mechanism release tab 20 is pivotably connected to the body of driving mechanism housing 10. The hollow tube driving mechanism release tab comprises two protrusions extending from the central pivoting body, one of which (212) engages groove 182 and one of which extends above driving mechanism housing 10 used for handling.

Figure 8A:
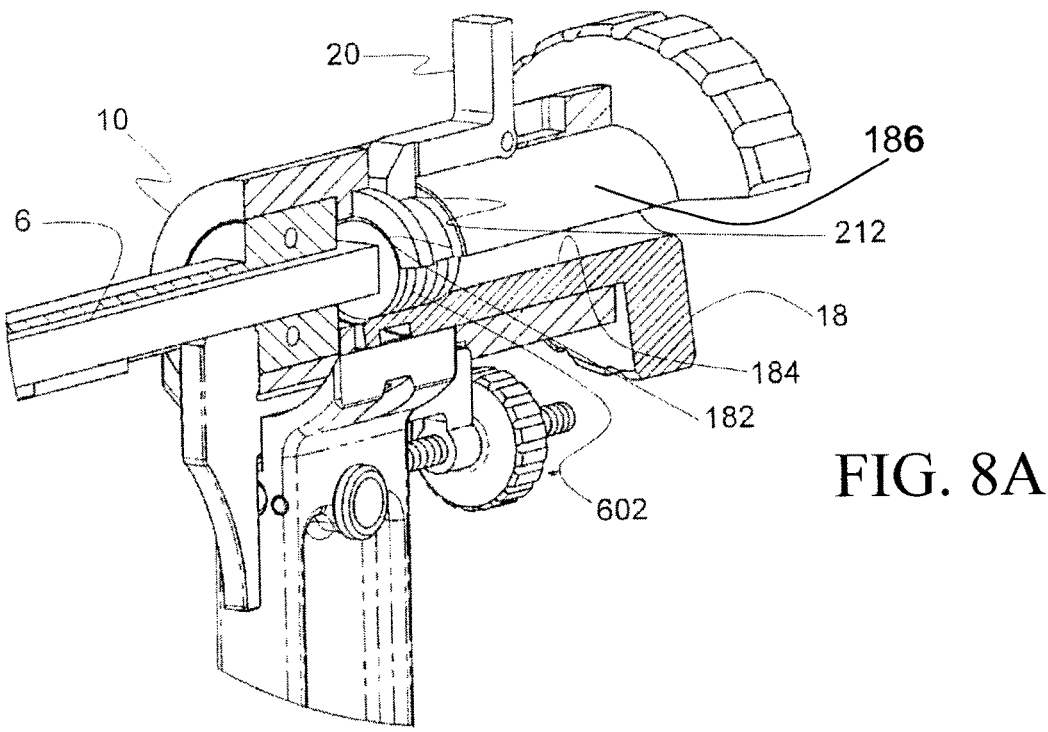
FIG. 8 presents isometric views of the rigid hollow tube control according to a preferred embodiment of the invention.

FIG. 8A shows a view of the hollow tube control as it appears when the driving mechanism release tab 20 is in its engaged position. In this configuration, protrusion 212 prevents handle 18 from moving along the distal-proximal axis of the body, so rotation of the handle causes threaded rod 602 to travel along the length of the shaft, thereby driving hollow tube actuator 6 and, via the remainder of the hollow tube driving mechanism (not shown in FIG. 8) engaged by actuator 6, slidable member (e.g., 2 and 4) and hollow tube 34 such that the distance through which the hollow tube moves is proportional to the angle through which knob 18 is rotated. In FIG. 8A, the threaded rod is shown at the most distal point of its travel; further movement of the threaded rod is blocked by the distal wall of driving mechanisms housing 10.

Figure 8B:
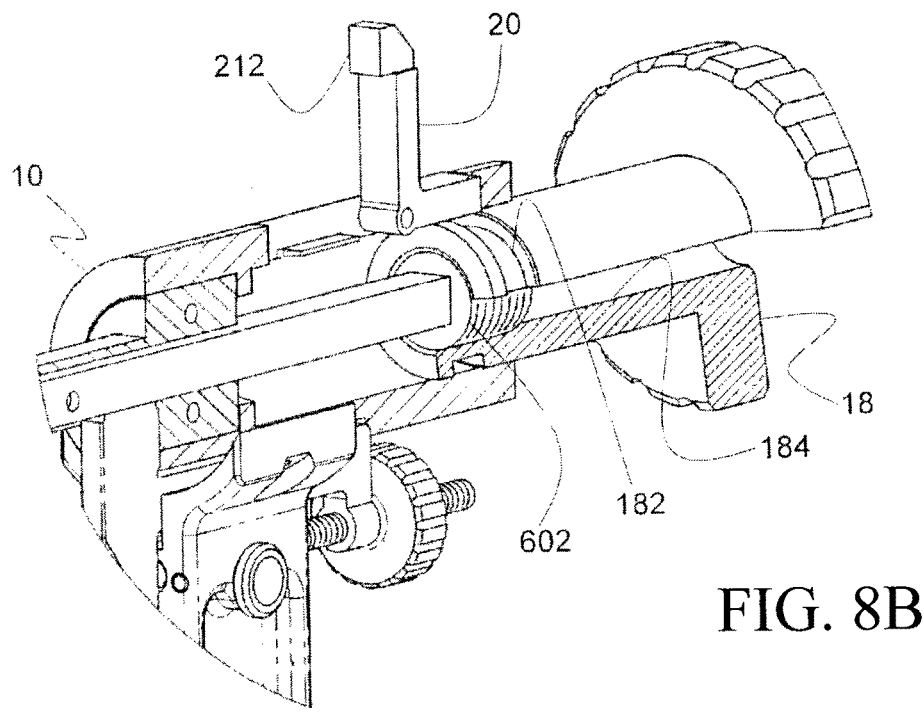

Application of pressure to its external protrusion activates tab 20, moving protrusion 212 to its disengaged position. FIG. 8B shows the hollow tube control with tab 20 in its disengaged position. Since in this configuration motion of knob 18 along the distal-proximal axis of the tool is unhindered, it is possible in this case to move hollow tube 34 by pushing or pulling knob 18 without turning it. By pulling knob 18 to the proximal direction hollow tube 34 is retrieved back into 90.

Reference is now made to FIG. 9, which presents isometric views illustrating the support element control according to a preferred embodiment of the invention. FIG. 9A shows an external view, while FIGS. 9B and 9C illustrated the internal mechanism of the support element control with handle 12 removed. In the embodiment of the support element control illustrated in FIG. 9, it comprises a threaded rod 24 and a quick-release pin 16. Quick-release pin 16 is adapted such that when it is in its disengaged position (as in FIG. 9B), motion of the threaded rod (both axial and rotational) is blocked, while when it is in its engaged position (as in FIG. 9C), motion of the threaded rod is permitted.

The support element control further comprises rotatable knob 14, which comprises an internally-threaded orifice that engages the threads of threaded rod 24. As with rotatable knob 18, in the most preferred embodiments, the circumference of knob 14 is knurled or provided with a plurality of indentations or protrusions for ease of handling. The control also comprises a slider, which comprises a tab 22, a circular orifice 26 of internal diameter at least sufficient to provide a slip fit over threaded rod 24, and a rigid connector that attaches the orifice to the tab. Tab 22 comprises a portion 27 that slides along the underside of shaft 50 and a protrusion that extends below the shaft. The distal portion of In some embodiments of the circular tunneler/adjustable suture passer that comprise this embodiment of the support element control, the underside of shaft 50 comprises a slot that allows the protrusion to move freely along the proximal-distal axis of shaft 50; in other embodiments, shaft 50 comprises a track on the exterior of its underside in which tab 22 and those portions of the support element driving mechanism engaged thereby slide.

In the embodiment of the support element control illustrated in FIG. 9, it engages the support element driving mechanism as follows. As knob 14 is turned, it travels along the length of threaded rod 24. When the travel is in the distal direction, the knob will engage orifice 26, thereby causing tab 22 to move in the distal direction. As sliding portion 27 moves distally, it engages the proximal end of the support element driving mechanism (e.g. actuator 58), thereby causing the support element to extend. When the user wishes to retract the support element, knob 14 is turned in the opposite direction, causing it to travel proximally along threaded rod 24. This motion will then leave a gap between knob 14 and orifice 26. Tab 22 can then be moved in the proximal direction manually by application of pressure to the portion that extends beneath shaft 50.

As shown in FIG. 9B, when quick-release pin 16 is in its engaged position, it prevents threaded rod 24 from moving, either by physically holding it (e.g. via a retractable vise-like grip) or by engaging an indentation in the threaded rod. When pin 16 is disengaged, as shown in FIG. 9C, it no longer prevents movement of threaded rod 24. In a manner analogous to that of driving mechanism release tab 20, engagement of the quick-release pin permits the user to manually move the support element control without the necessity of turning knob 14.

Figure 10:
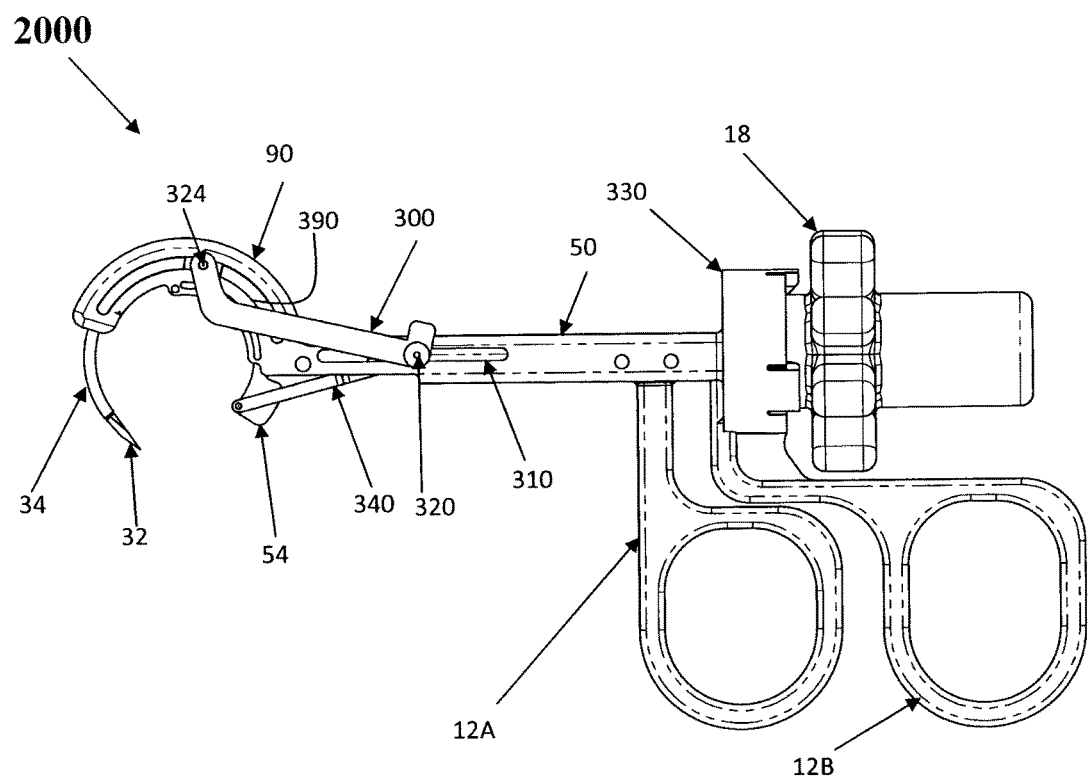
FIG. 10 presents a view of the curved/circular bone tunneling device or adjustable suture passer disclosed herein according to another embodiment of the invention.

Reference is now made to FIG. 10, which shows a view of a second embodiment 2000 of the circular tunneler/adjustable suture passer herein disclosed. The embodiment shown in FIG. 10 incorporates additional embodiments of the hollow tube and support element driving mechanisms and of the support element driving mechanism.

In the embodiment of the hollow tube driving mechanism shown in FIG. 10, shaft 50 incorporates body slot 330 along at least part of the length of at least one side of the body, and head 90 incorporates head slot 390 along at least part of the length of at least one side of the head. Slider 310 engages the hollow tube control at its proximal end. Yoke 300 is pivotably connected to slider 310 by pin 320 that passes through body slot 330, and is pivotably connected to the proximal end of hollow tube 34 by pin 324 that passes through head slot 390. When the hollow tube control is engaged, slider 310 travels distally, whereby yoke 300 forces hollow tube 34 to travel distally in proportion to the distance through which slider 310 has traveled. In this embodiment, the hollow tube control further comprises bearing housing 330.

FIG. 10 also shows a second embodiment of the support element driving mechanism. In this embodiment, the support element driving mechanism comprises an actuator 58 that engages at its proximal end the support element control and that is pivotably connected substantially at its distal end to a yoke 340 via a pin (not shown in FIG. 10). Yoke 340 is pivotably connected substantially at its distal end to the support element. When the support element control is engaged, actuator 58 travels distally, whereby yoke 340 moves downward, causing the support element to extend. In the embodiment shown in FIG. 10, handle 12 comprises two portions, a movable distal portion 12A and a stationary proximal portion 12B. In the embodiment shown, the handle is designed such that the user can grip it by placing his or her fingers through orifices at the bottom of the two portions of the handle. The movable distal portion of the handle further comprises a tab that fits into a slot in the underside of shaft 50.

In this embodiment, the support element control comprises the movable portion of the handle, which engages actuator 58; in preferred embodiments, the two are physically connected. As the movable portion of the handle is moved, actuator 58 moves in tandem, forcing yoke 340 to move and thereby extending or retracting the support element.

Figure 11A:
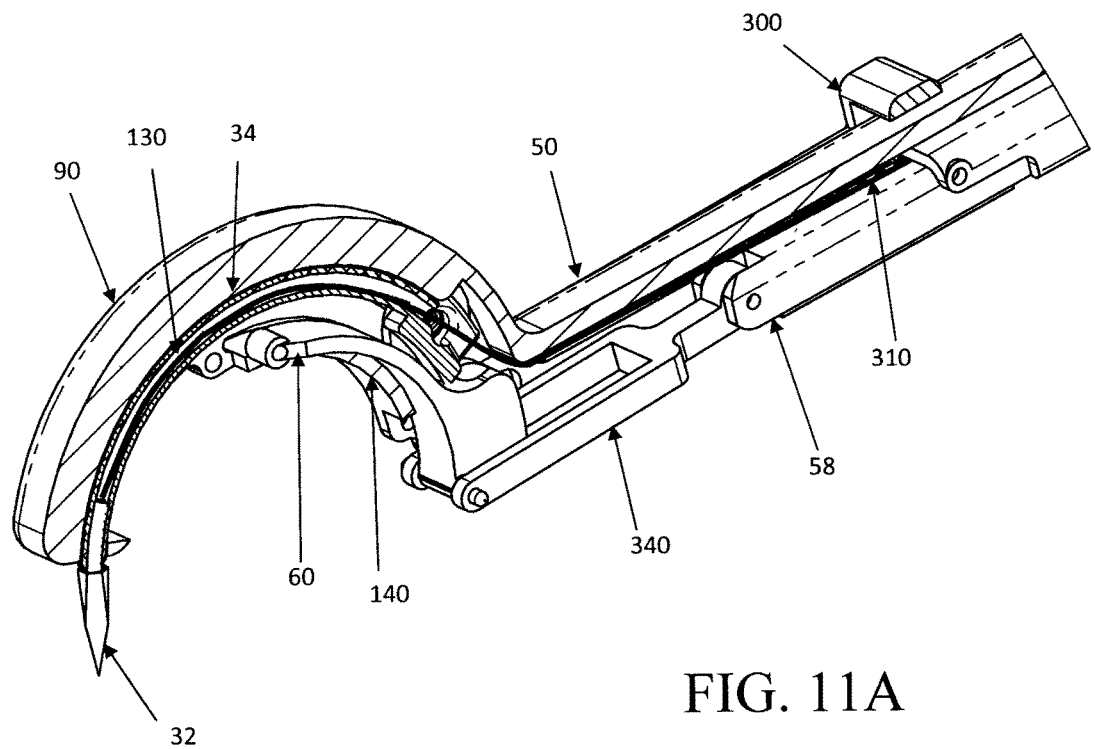
FIG. 11 presents interior views of the distal end of the curved/circular bone tunneling device or adjustable suture passer disclosed herein according to said second embodiment of the invention.
Figure 11B:
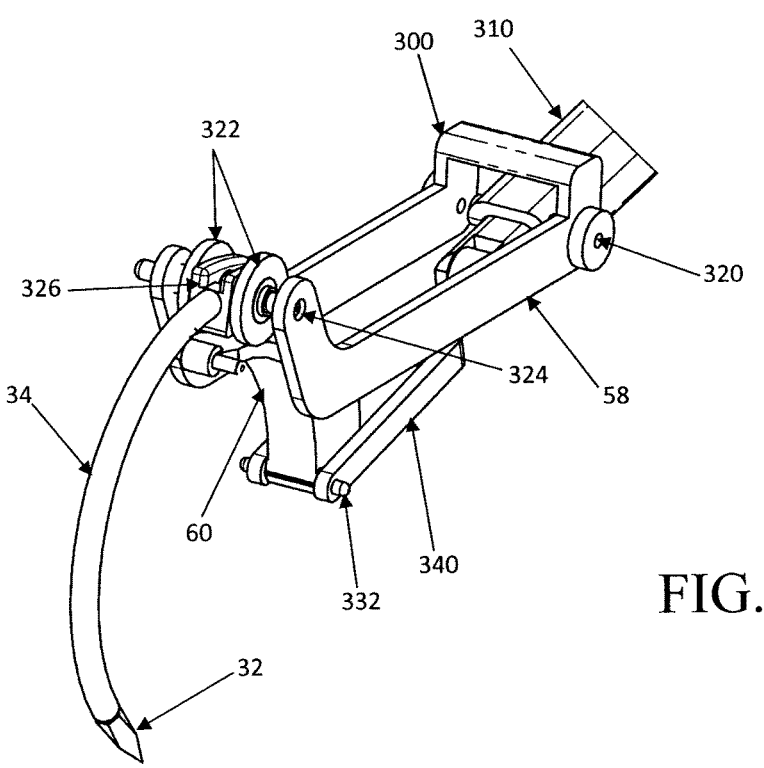

Reference is now made to FIG. 11, which shows views of the interior of the distal end of the circular tunneler/adjustable suture passer according to this second embodiment of the invention. The view shown in FIG. 11A illustrates how guide wire 130 passes through the head and shaft, and how the hollow tube actuator 58 engages yoke 340. FIG. 11B illustrates the workings of the support element driving mechanism according to this embodiment of the invention. When actuator 58 moves distally, it engages yoke 340. Substantially at its distal end, the yoke is connected to support element 54 via bearing 332. As the yoke descends in tandem with the motion of the actuator, the support element is pulled downward and forward, thus extending into its working position.

Figure 12A:
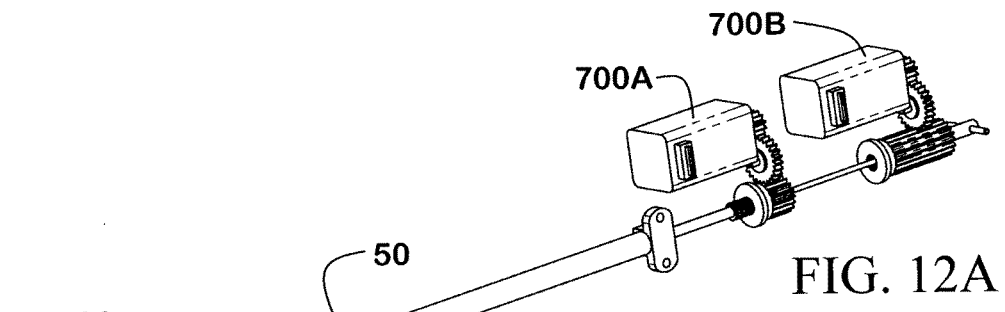
FIG. 12 presents a schematic view of a motorized control system for the curved/circular bone tunneling device or adjustable suture passer disclosed herein; and, FIG. 13 presents a schematic view of an embodiment of the present invention in which it further comprises a tendon holder.
Figure 12B:
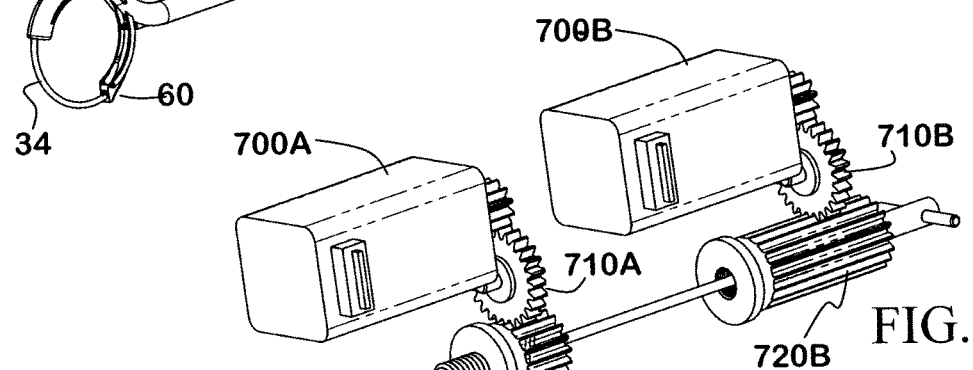
Figure 12C:
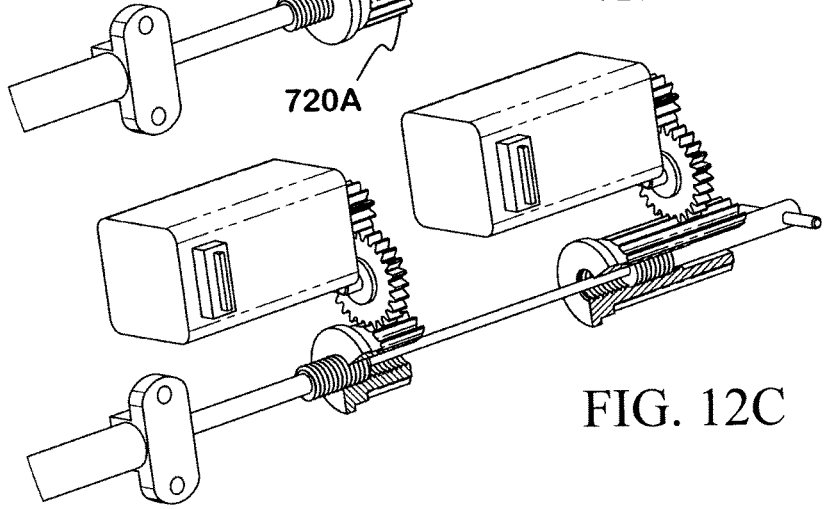

In the embodiments described thus far, the actuation of the device is performed manually. Reference is now made to FIG. 12, which presents a schematic illustration of an embodiment in which the hollow tube control and support mechanism control are actuated electrically. Motor 700 engages at least one of rotatable knobs 14 and 18. In the embodiment shown in the figure, each of the two rotatable knobs is engaged by a motor; motor 700A engages rotatable knob 14 and motor 700B engages rotatable knob 18. Any type of motor known in the art appropriate for actuating a medical device may be used. In preferred embodiments of the invention, motors 700A and 700B are DC stepper motors. FIG. 12A shows an overall schematic of such an embodiment. FIG. 12B presents a closer view of the hollow tube and support element controls. In these embodiments, rather than a knurled nut, each rotatable knob comprises a gear 720 (720A and 720B). Motors 700 (700A and 700B) drives gear 710 (710A and 710B, respectfully), which in turn drives gear 720 (720A and 710B, respectfully). FIG. 12C presents a cutaway view of the two rotatable knobs, illustrating the internal threads of the knobs and the threaded rods that the knobs engage, showing how the motor actuates the control mechanisms. Said gearing elements basically transforms the motors rotational input into two axial, linear, independent and juxtaposed moves.

In some embodiments of the invention, it further comprises a tendon holder. Any tendon holder known in the art that can be adapted for use with the present invention may be used.

The term "tendon holder" refers hereinafter to any device which enable the grasping of a tendon and pass of a suture through the same.

Figure 13A:
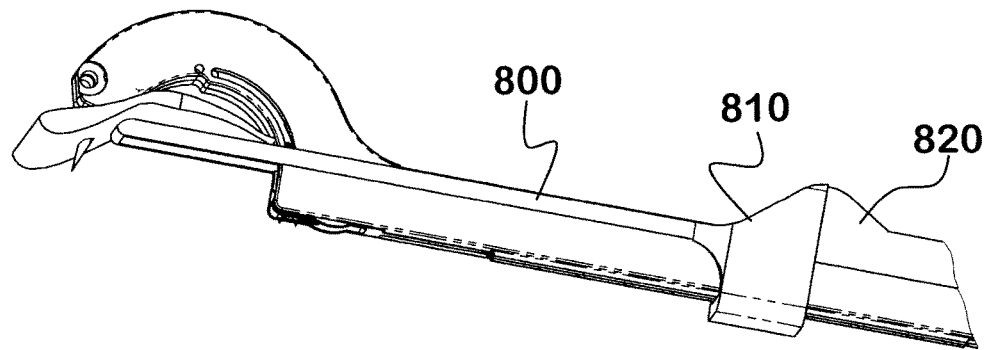

Reference is now made to FIG. 13, which illustrates a preferred embodiment of a tendon holder especially adapted for use with the invention herein disclosed. FIG. 13A presents a view of the distal portion of the circular bone tunneling device/suture passer showing the tendon holder. The tendon holder comprises grasping member 800, slider 810, and manipulator 820.

According to another embodiment, the tendon holder may comprise a single manipulator that enables both pushing and/or pulling movements.

Figure 13B:
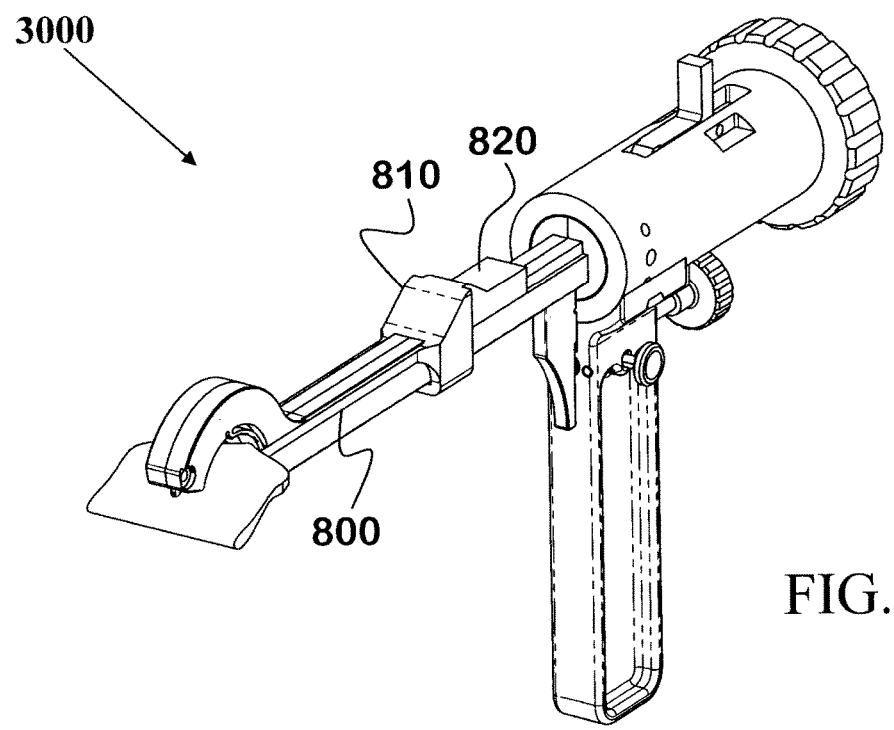

The slider is attached to the hollow elongate body of the circular tunneler/suture passer such that it can slide back and forth along the body. For example, it can comprise a channel with internal dimensions chosen to provide a slip fit over the body. Manipulator 820 is attached to the proximal side of the slider and sits on the upper side of the body. As can be seen in the diagram, in preferred embodiments, the manipulator has an ergonomic shape such that it can be pushed and pulled by the thumb of the operator of the device. Grasping member 800 is attached to the distal side of the slider. It is disposed on the upper side of the elongate body and slides along the distal-proximal axis of the body on the upper side of the body and passes under the head at the point at which the head is attached to the body. As can be seen in the diagram, in preferred embodiments, it has an elongated shape (e.g. a parallelepiped that is wider than it is high) and has a length sufficient that when it is moved to the distal end of its travel, it reaches sufficiently close to the distal end of head 90 that a tendon can be grasped between the distal end of the grasping member and the underside of the head. In the most preferred embodiments, when the grasping member is retracted to the most proximal point of its travel, it does not extend beyond the end of the body of the circular bone tunneling device/suture passer. An overall view of an embodiment 3000 of the device that comprises a tendon holder is shown in FIG. 13B.

It is also within the scope of the invention to disclose a method for tunneling through a bone during arthroscopic surgery. The method comprises steps of (a) providing a curved bone tunneling device comprising: (i) a hollow elongated body defining a rigid circular arc; said hollow elongated body comprising a surgical needle adapted to tunnel through a bone along a path formed by said circular arc; and, (ii) an extendable and retractable support element, reconfigurable from at least one extended configuration to at least one retracted configuration; (b) positioning said hollow elongated body of said device adjacent to the circumference of a bone; (c) fixating said needle to said bone; (d) extending said retractable support element to a location along the path formed by said circular arc; thereby grasping said bone with said support element and said hollow elongated body at two points along the circumference of said bone; (e) actuating said hollow tube and said needle, thereby tunneling through said bone along said circular arc path; wherein said step of tunneling through said bone is performed without drilling.

It is also within the scope of the invention to disclose a method for attaching soft tissue such as a ligament to a bone without the use of an anchor. The method comprises the following steps. A guide wire is passed through a device capable of imparting sufficient force to a surgical needle such that the surgical needle will pass through bone. A surgical needle or lance is attached to the guide wire and then connected to the distal end of the device. The device is then inserted into position. A support element engages the bone through which the needle is to be inserted on a side of the bone opposite that into which the needle is to be engaged, i.e. it holds the bone from the side towards which it would tend to move when the needle hits the bone's surface. The device is then engaged, causing the needle (and the guide wire attached thereto) to pass through the bone. A suture is attached to the proximal end of the guide wire. The guide wire is pulled through the bone, carrying the suture with it. Once the suture has passed through the bone, the guide wire is detached and discarded.

Figure 14:
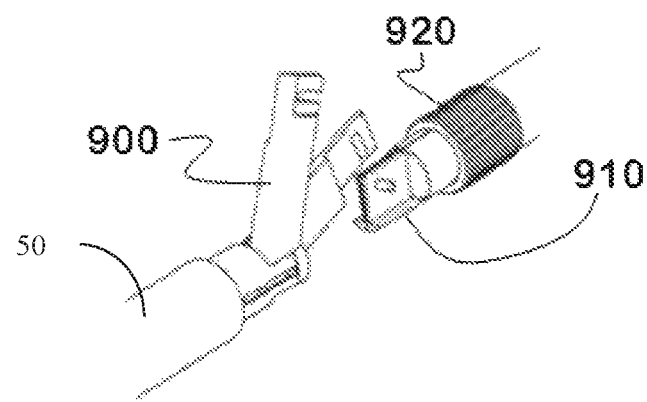
FIG. 14 presents a schematic view of an embodiment of the present invention, utilizing a motorized tool in which decoupling of the shaft is enabled.

Reference is now made to FIG. 14 which illustrates an embodiment in which the decoupling of the shaft (50) is enabled.

In other words, FIG. 14 presents a schematic view of a connector for rapid connection and disconnection of the shaft. Such a connector is particularly useful for embodiments that comprise motorized control.

In some embodiments of the invention in which it the circular bone tunneling device mechanically driven by one or more motors, it may include a connector for rapid connection and disconnection of the working portion of the circular bone tunneling device/suture passer (i.e. the head and the elongate body) from the shaft that contains the hollow tube and support mechanism controls.

Reference is now made again to FIG. 14, which illustrates an example of such a connector. The connector is hollow to allow physical connection of the control and driving mechanisms within the same, and comprises at least one pivotable joint 900. The pivotable joint 900 comprises a slot, a fixed acceptor 910 with a pin adapted to match the slot, and a slidable closure 920 that slides over the joint and pin after the connection is made (so as to fix the connection).

It should be understood to one skilled in the art that the design (e.g., cross section, length et cetera) and properties (e.g., mechanical properties; rigid or soft) of the surgical needle used is of critical importance in order to successfully enable the penetration of the needle into the bone.

As mentioned above, one of the needle's critical properties is the length of the needle used. If the needle used is too long, changing the direction of the penetration path by the hollow tube would be resisted and difficult to achieve.

According to another embodiment, the needle is a straight needle of slightly curved needle. According to another embodiment of the present invention the cross sectional area of the needle is selected from a group consisting of circular, triangular, rectangular or any combination thereof.

It should be understood to one skilled in the art that the design, (e.g., cross section, length et cetera) and properties (e.g., mechanical properties; rigid or soft, materials from which the same is made) of the surgical rigid hollow tube used is of critical importance in order to successfully enable the penetration of the same into the bone.

Figure 17:
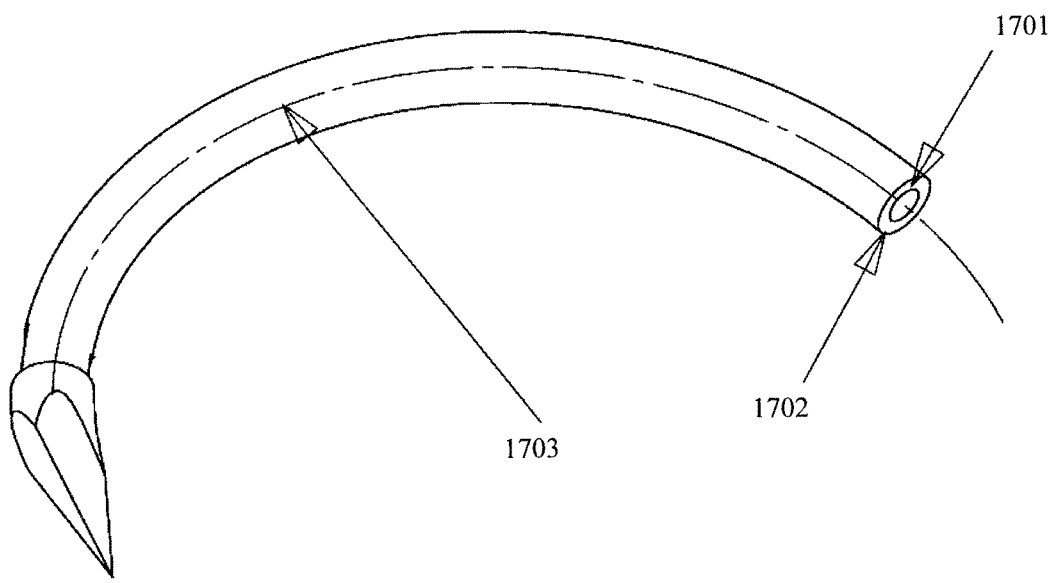
FIG. 17 schematically illustrates the hollow tubes's dimensions.

According to one embodiment of the present invention, the hollow tube's outer diameter is in the range of about 1 to about 3 mm; According to another embodiment, the internal diameter (through which the guide wire passes) is in the range of about 0.5 to about 1.5 mm; or any combination thereof. Reference is now made to FIG. 17 illustrating both the internal diameter (illustrated as numerical reference 1701) of the hollow tube and the outer diameter (illustrated as numerical reference 1702) of the same. Also illustrated in the figure is the radius of curvature (illustrated as numerical reference 1703). According to one embodiment of the present invention the radius of curvature 1703 is in the range of about 7.5 mm to about 15 mm, especially 12.5 mm. According to another embodiment, the surgical rigid hollow tube is made of biocompatible metal selected from hardened corrosion resistant steel.

Figure 15A:
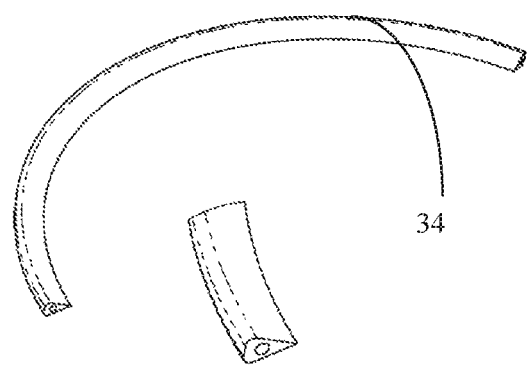
FIGS. 15a-15b presents a schematic view of an embodiment of the present invention, utilizing a hollow tube having a combination circular and triangular cross sectional area.

Reference is now made to FIG. 15*a* illustrating a hollow tube 34 having a triangular cross-section.

Figure 15B:
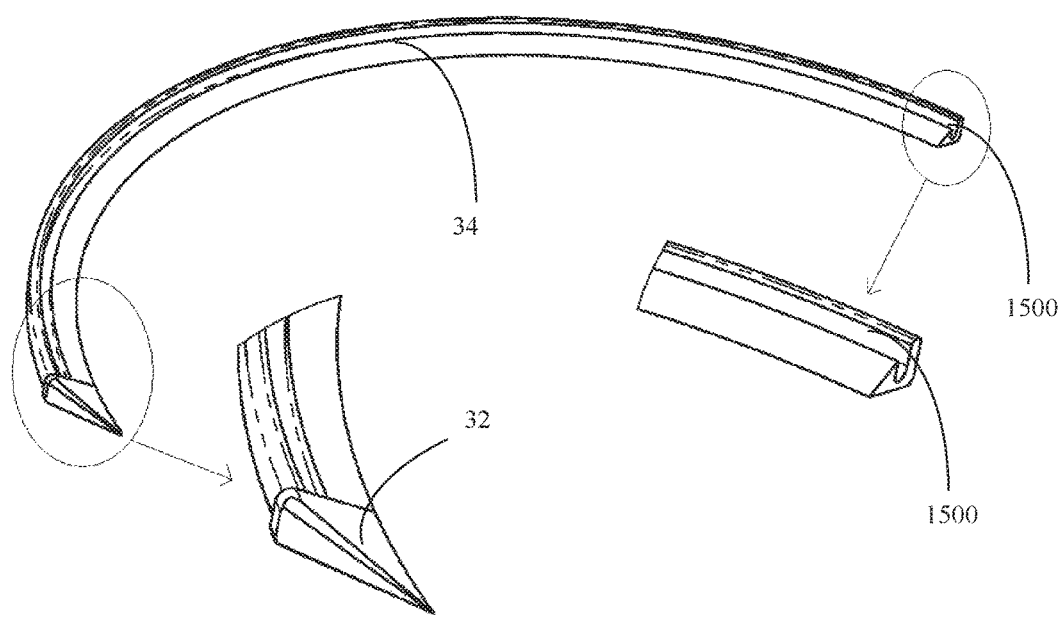

It should be pointed out that according to one embodiment of the present invention wire 130 is threaded through the hollow tube 34. According to another embodiment, the hollow tube 34 and the surgical needle comprises a groove along said needle's circumference (incase the cross section of said hollow tube is circular) or along at least one of said hollow tube's rib (in case the cross section is triangular or rectangular) throughout which said wire 130 is threaded. It should be understood to one skilled in the art, that the formation of a groove along one of the circumference or ribs simplifies the production line of the same. Reference is now made to FIG. 15b illustrating such an embodiment. According to this embodiment wire 130 is along groove 1500.

According to one embodiment of the present invention, one of the triangle's vertexes is pointing towards the center of the circular arc. Such an embodiment will ensure minimal resistance during the penetration into the bone.

Figure 16A:
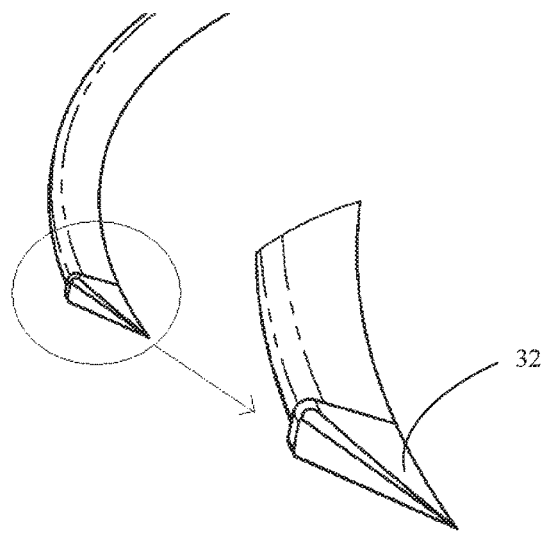
FIGS. 16a-16b illustrates another embodiment of the present invention, utilizing a slightly curved needle.
Figure 16B:
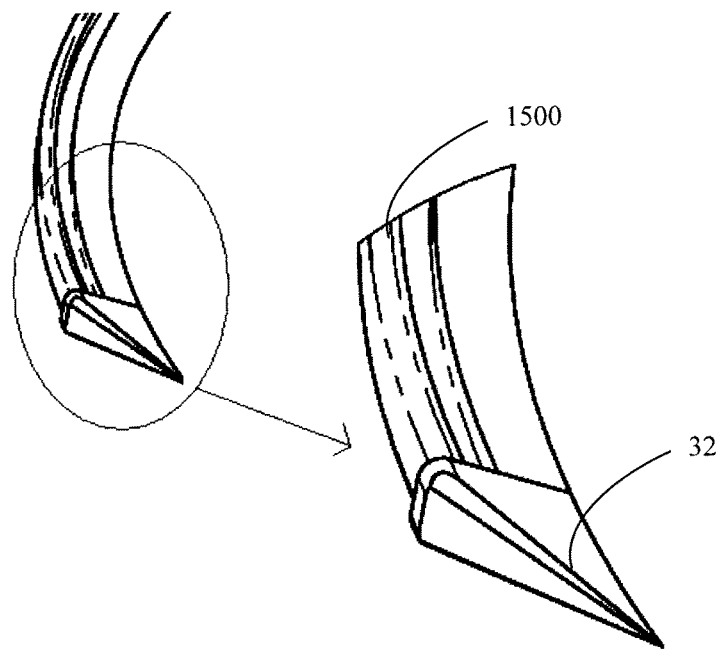

Reference is now made to FIGS. 16a-16b, illustrating another embodiment of the present invention in which the needle 32 being used is a slightly curved needle. Such curved, needle ensures the mating and the slip fit between the needle, 32, and the support element 54 and further allows the needle and hollow tube to move in the direction of the arc.

FIG. 16b also illustrates an embodiment in which the hollow tube 34 comprises a grove 1500 along which said wire 130 is threaded.

It should be understood to one skilled in the art that the design (e.g., cross section, length et cetera) and properties (e.g., mechanical properties; rigid or soft, materials from which the same is made) of the surgical rigid hollow tube used is of critical In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. A circular bone tunneling device, for use in arthroscopic surgery, comprising:
   a hollow elongate body comprising a hollow elongate body head, said hollow elongate body head enclosing a surgical needle adapted to tunnel through a bone along a circular path defined as a rigid circular arc;
   an extendable and retractable support element, movable between at least one extended configuration and at least one retracted configuration in which a distal end of said support element is located adjacent to a proximal end of said hollow elongate body head;
   a support element driving mechanism, adapted, upon activation of a support element control, to drive the motion of said support element; and
   at least one support element control adapted to control the movements of said support element driving mechanism, said support element control comprising:
   a threaded rod;
   a rotatable handle with a threaded orifice through which said threaded rod passes;
   a quick release pin having an engaged configuration and a disengaged configuration, adapted to permit motion of said threaded rod when in said engaged configuration and to prevent motion of said threaded rod when in said disengaged configuration; and,
   a slider,
   said support element including a portion which is adapted to be located along said path defined by said rigid circular arc,
   said support element and said hollow elongate body head being adapted to engage said bone at at least two points along the circumference of said bone.

2. The circular bone tunneling device according to claim 1, wherein said surgical needle is a rigid surgical needle.

3. The circular bone tunneling device according to claim 1 additionally comprising a rigid circular hollow tube adapted to be reversibly attached to said needle and to carry at least one guide wire, said rigid circular hollow tube movably disposed at least partially within said hollow body such that said rigid circular hollow tube can move through an orifice in said hollow elongate body head.

4. The circular bone tunneling device according to claim 3, additionally comprising:
   a rigid circular hollow tube driving mechanism operative to control the motion of said rigid circular hollow tube; and
   at least one rigid circular hollow tube control adapted to control the movements of said rigid circular hollow tube driving mechanism.

5. The circular bone tunneling device according to claim 1, wherein said surgical needle is sufficiently rigid so that its shape is maintained as it penetrates said bone along said circular arc.

6. The circular bone tunneling device according to claim 1, additionally comprising a surgical needle driving mechanism operative to control the motion of said surgical needle.

7. The circular bone tunneling device according to claim 6, wherein said surgical needle driving mechanism is operated independently of said support element.

8. The circular bone tunneling device according to claim 6, wherein upon activation of said surgical needle driving mechanism, said surgical needle is moved along said circular path to penetrate said bone.

9. The circular bone tunneling device according to claim 1, wherein the extendable and retractable support element is adapted to reach, upon extension, a predetermined location at which it intersects said circular path.

10. The circular bone tunneling device according to claim 1, additionally comprising a handle adapted for driving said surgical needle to tunnel through said bone along said circular path.

11. The circular bone tunneling device according to claim 1, further incorporating an indicator for indicating the extent of travel, along said arc, of said surgical needle.

* * * * *